US011712376B2

(12) United States Patent
Ninomiya et al.

(10) Patent No.: US 11,712,376 B2
(45) Date of Patent: Aug. 1, 2023

(54) ABSORBENT ARTICLE AND METHOD AND DEVICE FOR MANUFACTURING ABSORBENT ARTICLE

(71) Applicant: UNICHARM Corporation, Ehime (JP)

(72) Inventors: Akihide Ninomiya, Kagawa (JP); Masaharu Tomioka, Kagawa (JP)

(73) Assignee: Unicharm Corporation, Ehime (JP)

( * ) Notice: Subject to any disclaimer, the term of this patent is extended or adjusted under 35 U.S.C. 154(b) by 835 days.

(21) Appl. No.: 16/548,609

(22) Filed: Aug. 22, 2019

(65) Prior Publication Data
US 2019/0374404 A1    Dec. 12, 2019

Related U.S. Application Data

(63) Continuation of application No. PCT/JP2017/006897, filed on Feb. 23, 2017.

(51) Int. Cl.
*A61F 13/49* (2006.01)
*A61F 13/15* (2006.01)
(Continued)

(52) U.S. Cl.
CPC .. *A61F 13/49019* (2013.01); *A61F 13/15699* (2013.01); *A61F 13/15739* (2013.01);
(Continued)

(58) Field of Classification Search
CPC .......... A61F 13/49019; A61F 13/15699; A61F 13/15739; B32B 37/18; B32B 38/0004
See application file for complete search history.

(56) References Cited

U.S. PATENT DOCUMENTS

| 11,351,067 B2* | 6/2022 | Ninomiya ......... A61F 13/15764 |
| 2010/0076394 A1* | 3/2010 | Hayase ............. A61F 13/49019 604/385.29 |

(Continued)

FOREIGN PATENT DOCUMENTS

| CN | 105853067 A | 8/2016 |
| CN | 106029029 A | 10/2016 |

(Continued)

OTHER PUBLICATIONS

Office Action issued in corresponding Chinese Patent Application No. 201780087106.1, dated Mar. 23, 2021 (11 pages).

(Continued)

*Primary Examiner* — George R Koch
*Assistant Examiner* — Christopher C Caillouet
(74) *Attorney, Agent, or Firm* — Osha Bergman Watanabe & Burton LLP

(57) ABSTRACT

An absorbent article having a lateral direction, a vertical direction, and a front-rear direction that are orthogonal to each other is provided. The absorbent article includes: a first sheet-like member; a second sheet-like member; elastic members that are inserted along the lateral direction between a pair of mutually-opposing facing surfaces of the first sheet-like member and that are spaced apart in the vertical direction; joining portions that join the pair of mutually-opposing facing surfaces and that are spaced part in the lateral direction and in the vertical direction; and side-seal sections disposed at each lateral end portion of the absorbent article. The joining portions are formed on two sides of the elastic members in the vertical direction so that the elastic members are sandwiched and pressed between the joining portions on the two sides.

11 Claims, 18 Drawing Sheets

(51) Int. Cl.
  *B32B 38/00* (2006.01)
  *B32B 37/18* (2006.01)
(52) U.S. Cl.
  CPC .......... *A61F 13/4902* (2013.01); *B32B 37/18* (2013.01); *B32B 38/0004* (2013.01); *A61F 2013/15869* (2013.01); *A61F 2013/15878* (2013.01); *A61F 2013/49025* (2013.01); *B32B 2555/02* (2013.01)

(56) References Cited

U.S. PATENT DOCUMENTS

| | | | |
|---|---|---|---|
| 2016/0331600 A1* | 11/2016 | Polidori | A61F 13/15739 |
| 2017/0007467 A1* | 1/2017 | Yamamoto | B29C 55/02 |

FOREIGN PATENT DOCUMENTS

| | | | | |
|---|---|---|---|---|
| CN | 106029030 | A | 10/2016 | |
| CN | 106137542 | A | 11/2016 | |
| EP | 2450015 | A1 | 5/2012 | |
| EP | 3092997 | A1 | 11/2016 | |
| EP | 3111900 | A1 | 1/2017 | |
| EP | 3127517 | A1 | 2/2017 | |
| JP | 2001-504899 | A | 4/2001 | |
| JP | 2008-131968 | A | 6/2008 | |
| JP | 2008-154998 | A | 7/2008 | |
| JP | 2009-106667 | A | 5/2009 | |
| JP | 2009148447 | A | 7/2009 | |
| JP | 2014-198179 | A | 10/2014 | |
| JP | 5997404 | B1 | 9/2016 | |
| WO | WO-2015129296 | A1 * | 9/2015 | A61F 13/15593 |

OTHER PUBLICATIONS

Office Action issued in corresponding European Patent Application No. 17897472.1, dated Jan. 24, 2020 (9 Pages).
International Search Report issued in corresponding International Application No. PCT/JP2017/006897, dated May 16, 2017 (6 pages).
Written Opinion issued in corresponding International Application No. PCT/JP2017/006897, dated May 16, 2017 (5 pages).
International Preliminary Report on Patentability issued in corresponding International Application No. PCT/JP2017/006897 dated Aug. 27, 2019 (8 pages).
Office Action issued in corresponding Chinese Patent Application No. 201780087106.1, dated Aug. 11, 2021 (6 pages).
Office Action issued in corresponding European Patent Application No. 17897472.1, dated Apr. 28, 2022 (56 Pages).
Office Action issued in corresponding European Patent Application No. EP 17897472.1 dated Feb. 14, 2023 (11 pages).

* cited by examiner

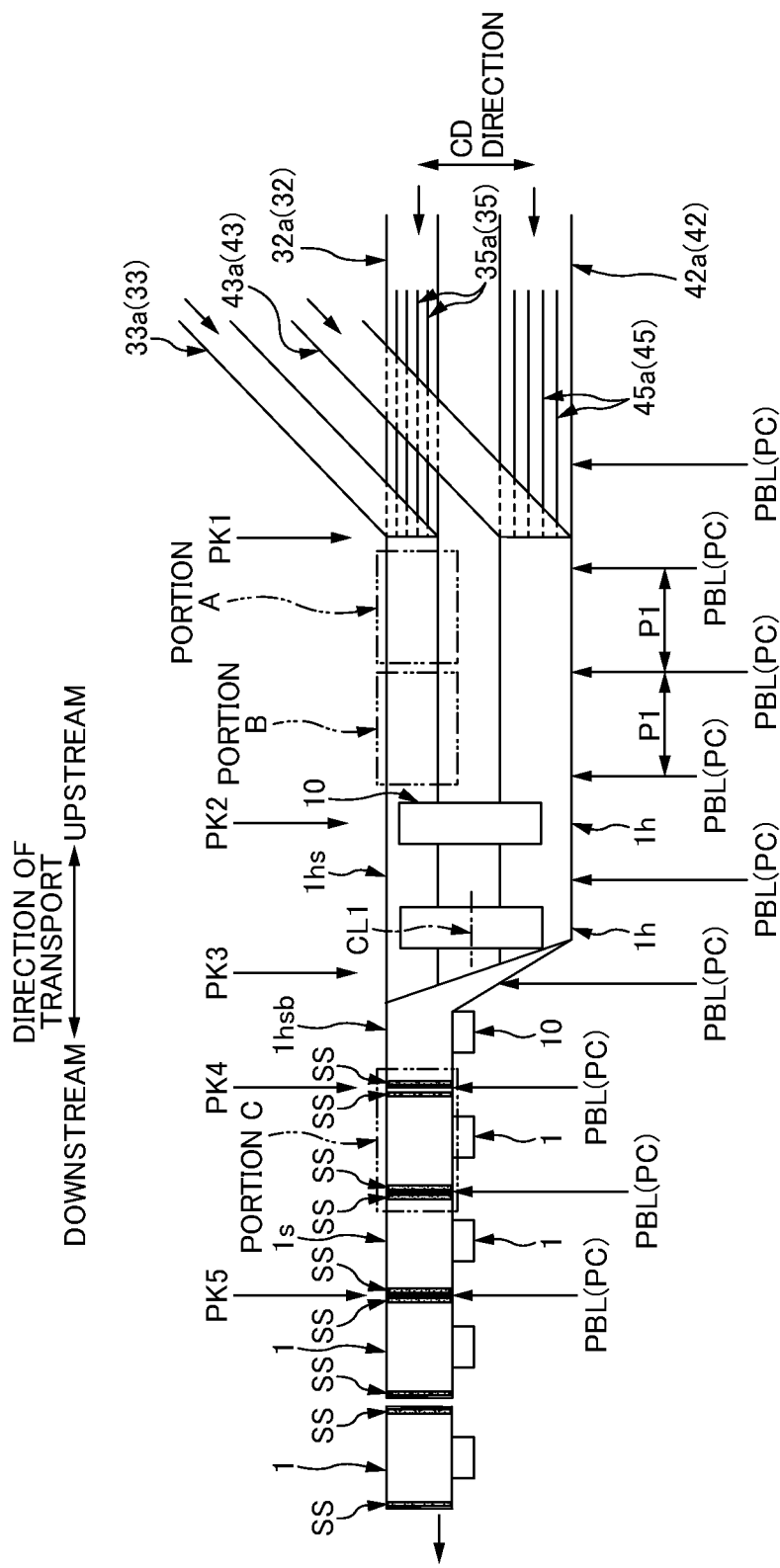

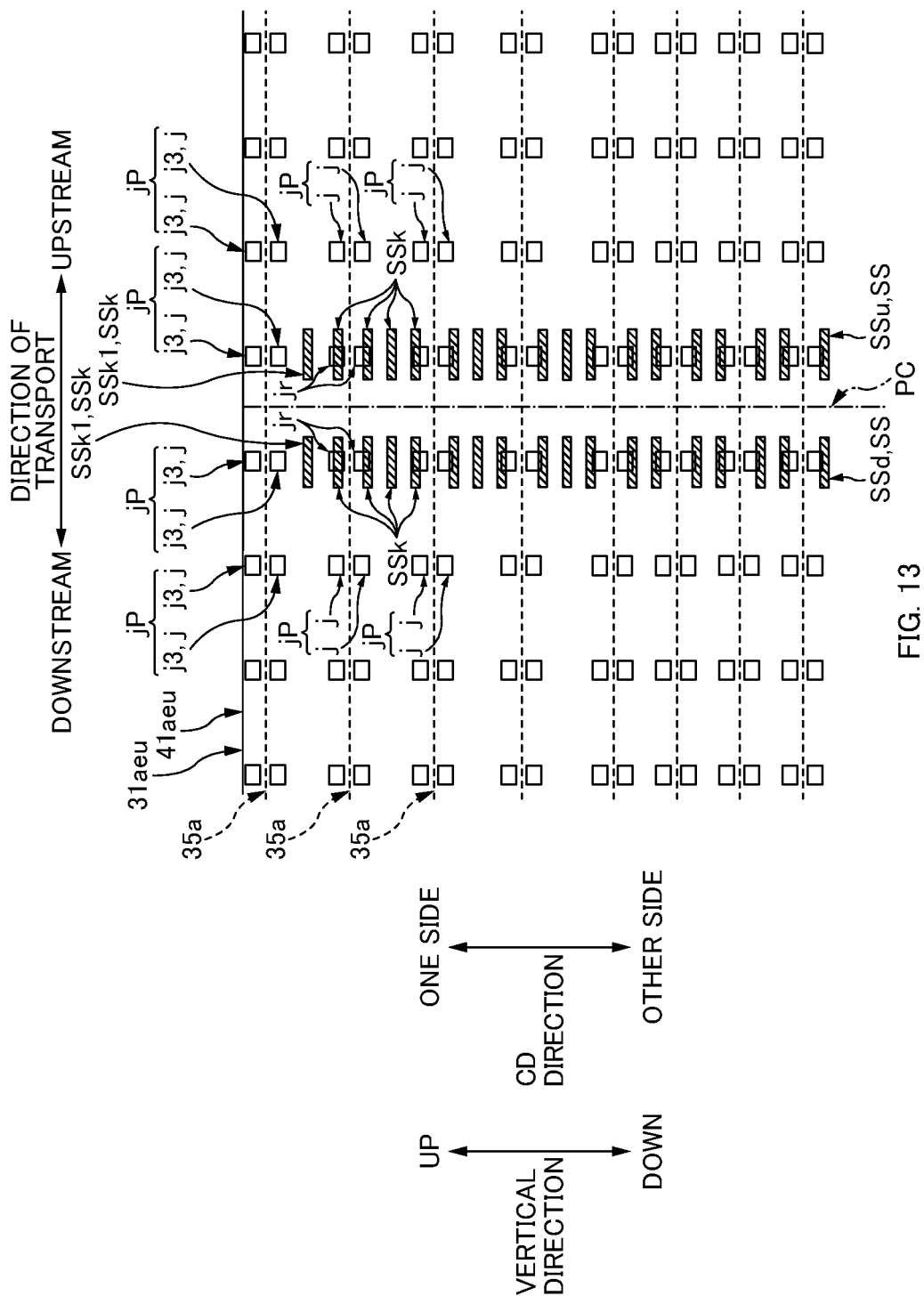

ABSORBENT ARTICLE AND METHOD AND DEVICE FOR MANUFACTURING ABSORBENT ARTICLE

TECHNICAL FIELD

The present invention relates to an absorbent article such as a disposable diaper and a method and a device for manufacturing the absorbent article.

BACKGROUND

A disposable diaper 1' shown in the schematic perspective view of FIG. 1A is a conventional example of an absorbent article that absorbs excrement such as urine. This diaper 1' includes a first sheet-like member 31' and a second sheet-like member 41' that have been given stretchability in the lateral direction by elastic members 35' attached thereto. And, the diaper 1' also includes side-seal sections SS' in end portions 31e' (41e') in the lateral direction, and in the side-seal sections SS', the two sheet-like members are welded together overlaid in the thickness direction, which intersects the lateral direction and the vertical direction.

The elastic members 35' are normally attached to the first sheet-like member 31' with use of an adhesive. However, when the elastic members 35' are attached with use of an adhesive, there is a risk that hardening of the adhesive at the outer circumferential surfaces of the elastic members 35' will impair the elasticity (i.e., stretchability) of the elastic members 35' and impair the softness of the first sheet-like member 31'. For this reason, in recent years, consideration has been given to the attachment of the elastic members 35' to the first sheet-like member 31' without using an adhesive, and the following is one example of such a method disclosed in PTL 1.

PATENT LITERATURE

[PTL 1] Japanese Unexamined Patent Application Publication (Translation of PCT Application) No. 2001-504899

FIGS. 1B and 1C are schematic plan views for describing the aforementioned method. In the enlarged view of FIG. 1C, the elastic members 35' contract in the direction of transport compared to FIG. 1B as will be described later, the direction-of-transport gaps between joining portions j' that are adjacent in the direction of transport are actually smaller than the direction-of-transport gaps between the joining portions j' in the enlarged view in FIG. 1B. But, for the sake of convenience, these gaps in FIG. 1C are shown at the same size as in FIG. 1B. The same follows for the enlarged views in FIGS. 6A and 6B that will be described later. The following describes the aforementioned method with reference to FIGS. 1B and 1C.

First, as shown in FIG. 1B, the first sheet-like-member continuous body 31a' is continuous in the direction of transport, and is transported with its direction of transport conforming to the lateral direction of the diaper 1'. Elastic-member continuous bodies 35a' are continuous in the direction of transport, and are inserted between a pair of mutually-opposing facing surfaces of the first sheet-like-member continuous body 31a' with stretched in the direction of transport.

Next, a plurality of joining portions j' for joining the pair of facing surfaces are formed at intervals in the direction of transport. At this time, the joining portions j' are formed at positions on two sides of the elastic-member continuous body 35a' with respect to a CD direction that intersects the direction of transport.

Subsequently, the first sheet-like-member continuous body 31a' is cut at cutting target positions PC' of the continuous body 31a' in the direction of transport, thus forming cutform-shaped first sheet-like members 31' having the elastic members 35' attached thereto as shown in FIG. 1C. Due to this cutting, the elastic members 35' that have been cut contract in the direction of transport and attempt to expand in the CD direction. But here, the expansion of the elastic members 35' in the CD direction is restricted by the pairs of joining portions j' located on the two sides in the CD direction, and therefore the elastic members 35' are substantially sandwiched and pressed in the CD direction by the joining portions j'. As a result, the elastic members 35' are attached to the first sheet-like member 31'.

Also, as shown in FIG. 1C, when cutting is performed at the cutting target positions PC', the second sheet-like-member continuous body 41a' has already been overlaid on the first sheet-like-member continuous body 31a', and the side-seal sections SS' have already been formed on the two sides of the cutting target positions PC' in the direction of transport. Accordingly, after the first sheet-like members 31a' are produced by the cutting at the cutting target positions PC', each first sheet-like member 31a' is provided with the two side-seal sections SS' in the respective lateral end portions 31e'; at this time the lateral direction conforms the direction of transport.

Also, in the diaper 1' in the state shown in FIG. 1A, a region R31' of the first sheet-like member 31' that is laterally inward of the side-seal sections SS' comes into contact with the stomach side of the wearer's torso. For this reason, this inward region R31' needs to be given with stretchability in the lateral direction. In the case where the joining portions j' are not provided in the side-seal sections SS' and laterally outside of the side-seal sections SS' as shown in the partial enlarged view in FIG. 1A, when the cutting at the cutting target positions PC' (FIG. 1C) causes the elastic members 35' to contract in the lateral direction (the direction of transport), there is a risk that end portions 35e' of the elastic members 35' will not stop at positions laterally outside the inward region R31', but rather will move into the inward region R31' as shown in the partial enlarged view of FIG. 1A. If this happens, some portions in lateral end portions R31e' of the inward region R31' will lose stretchability, which originally should be given to the portions. Thus, the diaper 1' will become an unsuitable product in terms of stretchability.

SUMMARY

One or more embodiments suppress the formation of a portion that does not have stretchability in a region of a first sheet-like member that is laterally inward of side-seal sections, the first sheet-like member pertaining to an absorbent article.

According to one or more embodiments, a method for manufacturing an absorbent article is provided. The absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, and the thickness direction being a direction that intersects the lateral direction. The method includes:

an arranging step of arranging a plurality of elastic-member continuous bodies between a pair of mutually-opposing facing surfaces of a first sheet-like-member continuous body that is being transported,
  a direction of transport of the first sheet-like-member continuous body conforming to the lateral direction,
  the plurality of elastic-member continuous bodies being continuous in the direction of transport,
  the first sheet-like-member continuous body being continuous in the direction of transport,
  the plurality of elastic-member continuous bodies being in a stretched state in the direction of transport and being placed side-by-side spacing in a CD direction,
  the CD direction intersecting the direction of transport and the thickness direction;
a joining-portion forming step of forming a plurality of joining portions spacing in the direction of transport and the CD direction,
  the joining portions joining the pair of facing surfaces of the first sheet-like-member continuous body to each other,
  the joining-portion forming step including forming the plurality of joining portions on two sides of the elastic-member continuous bodies in the CD direction while maintaining the elastic-member continuous bodies in a state of being stretched in the direction of transport,
  the joining portions being formed so that, by direction-of-transport contraction and CD-direction expansion of the elastic member after a cutting step, the elastic member is sandwiched and pressed in the CD direction by the joining portions on the two sides, being attached to the first sheet-like member,
  the joining portions being formed so that a portion of at least one of the joining portions is overlapped with at least a portion of the side-seal section in a view of the first sheet-like-member continuous body in the thickness direction;
an overlaying step of overlaying, in the thickness direction, a second sheet-like-member continuous body on the first sheet-like-member continuous body in which the joining portions have been formed,
  the second sheet-like-member continuous body being continuous in the direction of transport;
a side-seal-section forming step of forming the side-seal section on each of two sides of each of cutting target positions in the direction of transport,
  the cutting target positions being set at a predetermined pitch in the direction of transport,
  the first sheet-like-member continuous body and the second sheet-like-member continuous body that have been overlaid on each other in the thickness direction being welded together in the side-seal section; and
  the cutting step of producing the absorbent article that has the elastic member, the first sheet-like member, and the second sheet-like member,
    the cutting step being performed after the side-seal-section forming step and by cutting the first sheet-like-member continuous body, the elastic-member continuous bodies, and the second sheet-like-member continuous body at each of the cutting target positions.

Further, according to one or more embodiments, a device for manufacturing an absorbent article is provided. The absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, and the thickness direction being a direction that intersects the lateral direction. The device includes:

an arranging device configured to arrange a plurality of elastic-member continuous bodies between a pair of mutually-opposing facing surfaces of a first sheet-like-member continuous body that is being transported,
  a direction of transport of the first sheet-like-member continuous body conforming to the lateral direction,
  the plurality of elastic-member continuous bodies being continuous in the direction of transport,
  the first sheet-like-member continuous body being continuous in the direction of transport,
  the plurality of elastic-member continuous bodies being in a stretched state in the direction of transport and being placed side-by-side spacing in a CD direction,
  the CD direction intersecting the direction of transport and the thickness direction;
a joining-portion forming device configured to form a plurality of joining portions spacing in the direction of transport and the CD direction,
  the joining portions joining the pair of facing surfaces of the first sheet-like-member continuous body to each other,
  the joining-portion forming device forming the plurality of joining portions on two sides of the elastic-member continuous bodies in the CD direction while maintaining the elastic-member continuous bodies in a state of being stretched in the direction of transport,
  the forming is performed so that, by direction-of-transport contraction and CD-direction expansion of the elastic member at a position downstream the direction of transport with respect to a cutting device, the elastic member is sandwiched and pressed in the CD direction by the joining portions on the two sides, being attached to the first sheet-like member,
  the forming is performed so that a portion of at least one of the joining portions is overlapped with at least a portion of the side-seal section in a view of the first sheet-like-member continuous body in the thickness direction;
an overlaying device configured to overlay, in the thickness direction, a second sheet-like-member continuous body on the first sheet-like-member continuous body in which the joining portions have been formed,
  the second sheet-like-member continuous body being continuous in the direction of transport;
a side-seal-section forming device configured to form the side-seal section on each of two sides of each of cutting target positions in the direction of transport,
  the cutting target positions being set at a predetermined pitch in the direction of transport,
  the first sheet-like-member continuous body and the second sheet-like-member continuous body that have been overlaid on each other in the thickness direction being welded together in the side-seal section; and
  the cutting device configured to produce the absorbent article that has the elastic member, the first sheet-like member, and the second sheet-like member,
    at a position downstream in the direction of transport with respect to the side-seal-section forming device, the cutting device cutting the first sheet-like-member continuous body, the elastic-member continuous bodies, and the second sheet-like-member continuous body at each of the cutting target positions.

Further, according to one or more embodiments, an absorbent article having a lateral direction, a vertical direction, and a front-rear direction that are orthogonal to each other is provided. The absorbent article includes:

a first sheet-like member;

a second sheet-like member;

a plurality of elastic members that are inserted along the lateral direction between a pair of mutually-opposing facing surfaces of the first sheet-like member, and that are arranged spacing in the vertical direction;

a plurality of joining portions that are for joining together the pair of facing surfaces and that are arranged with spacing in the lateral direction and in the vertical direction, the joining portions being formed on two sides of the elastic members in the vertical direction so that the elastic members are sandwiched and pressed between the joining portions on the two sides; and a side-seal section that is provided in each lateral end portion, a portion of at least one of the joining portions being overlapped with at least a portion of the side-seal section in a view of the first sheet-like member in the front-rear direction the first sheet-like member and the second sheet-like member being overlaid in the front-rear direction and welded in the side-seal section.

Features of one or more embodiments of the present invention other than the above will become clear by reading the description of the present specification with reference to the accompanying drawings.

According to one or more embodiments of the present invention, it is possible to suppress the formation of a portion that does not have stretchability in a region of a first sheet-like member pertaining to an absorbent article that is laterally inward of side-seal sections.

BRIEF DESCRIPTION OF THE DRAWINGS

FIG. 8 is a schematic plan view showing a partial perspective view of how the diaper 1 is manufactured in a manufacturing line.

FIG. 13 is a schematic view of a case where welded portions j (j3) are provided on one side in a CD direction of a welded portion SSk1 that is located farthest on the one side among welded portions SSk, SSk . . . in the side-seal section SS.

DETAILED DESCRIPTION

Figure 1A:
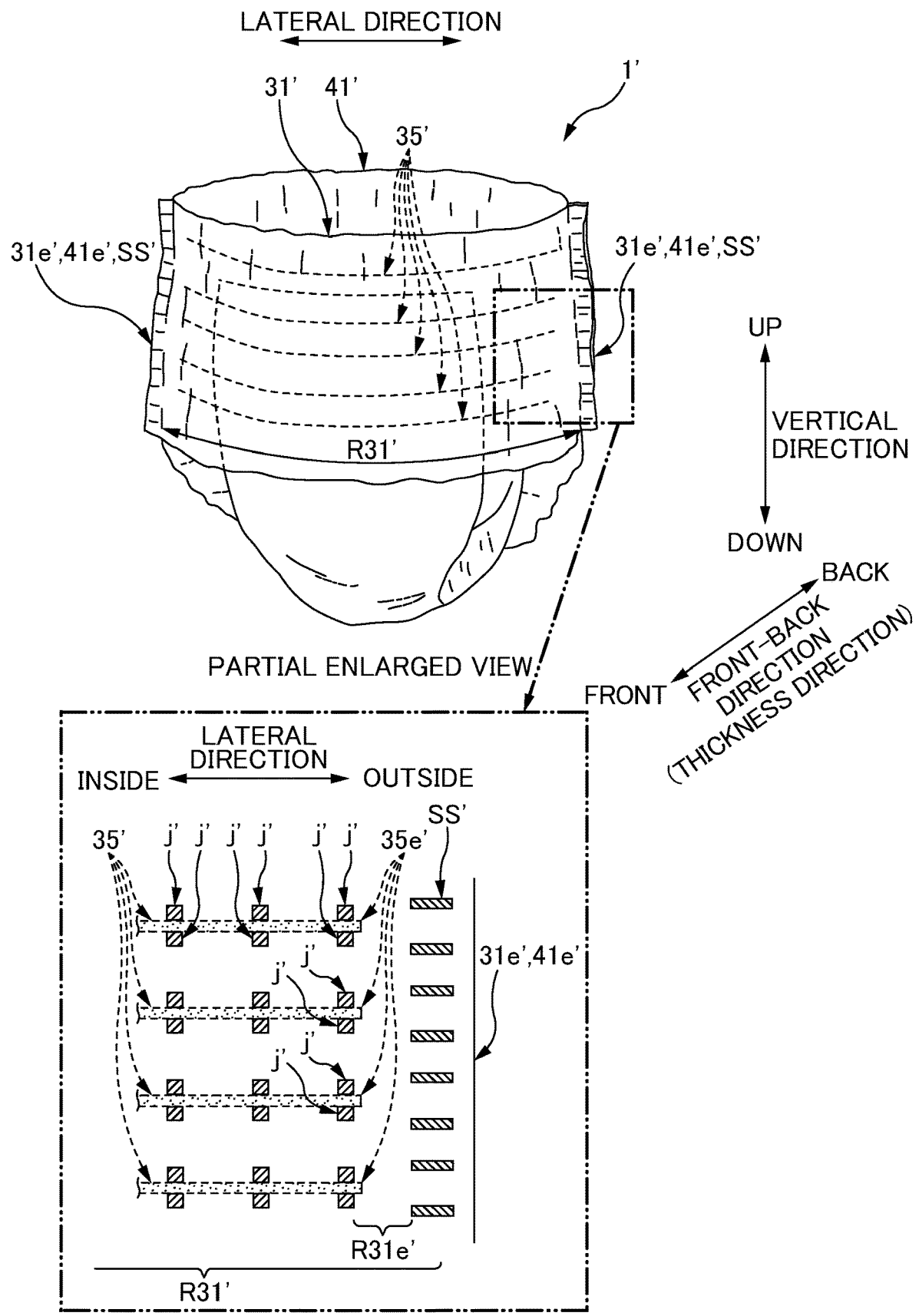
FIG. 1A is a schematic perspective view of a disposable diaper 1' as one example of an absorbent article.
Figure 1B:
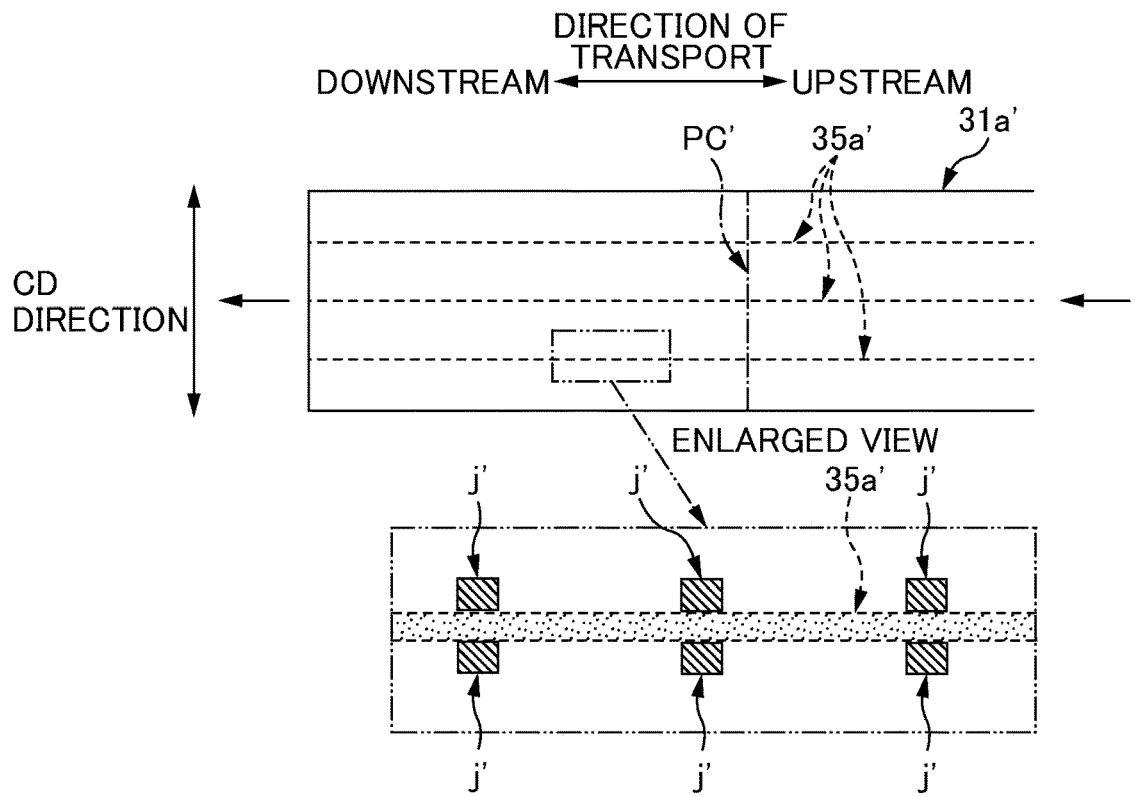
FIG. 1B is a diagram illustrating a method for attaching elastic members 35' to a first sheet-like member 31' pertaining to the diaper 1' without using an adhesive.
Figure 1C:
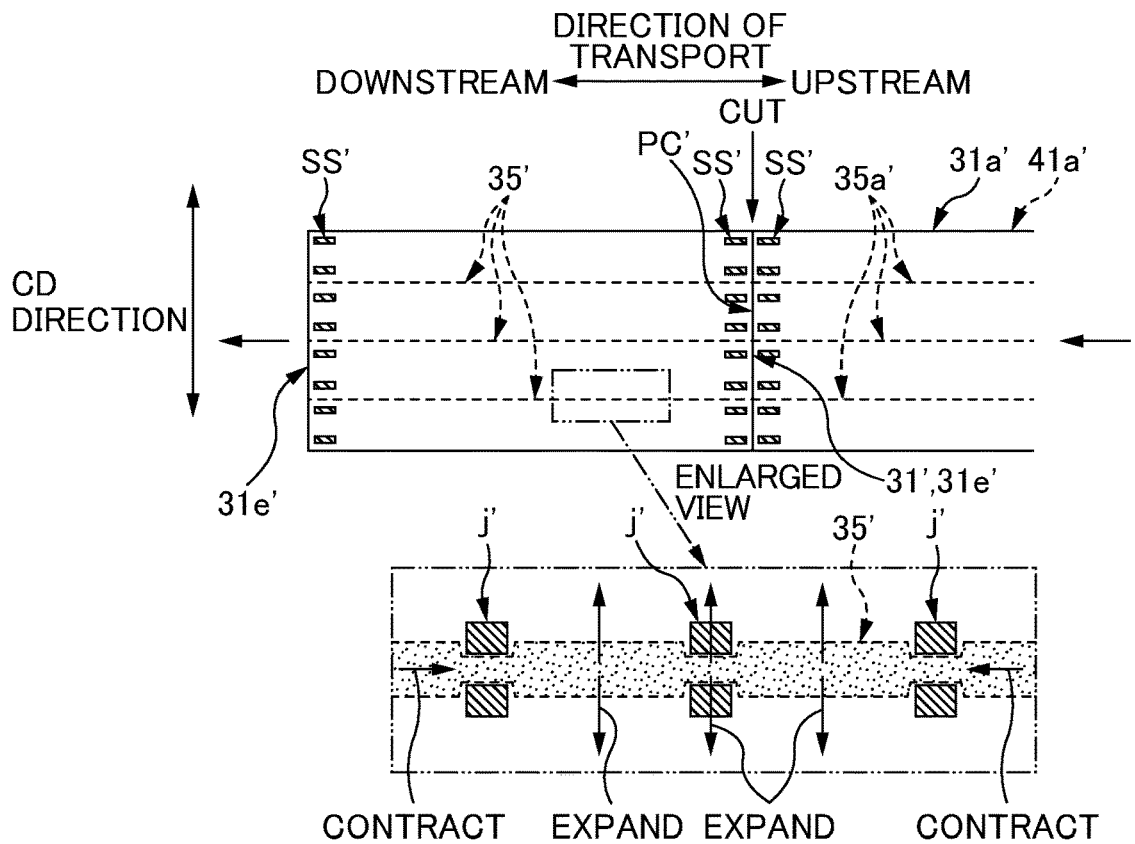
FIG. 1C is a diagram illustrating the above method.

At least the following matters will become clear with the description of this specification and the attached drawings.

A method for manufacturing an absorbent article, the absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, the thickness direction being a direction that intersects the lateral direction, the method including:

an arranging step of arranging a plurality of elastic-member continuous bodies between a pair of mutually-opposing facing surfaces of a first sheet-like-member continuous body that is being transported, a direction of transport of the first sheet-like-member continuous body conforming to the lateral direction, the plurality of elastic-member continuous bodies being continuous in the direction of transport, the first sheet-like-member continuous body being continuous in the direction of transport, the plurality of elastic-member continuous bodies being in a stretched state in the direction of transport and being placed side-by-side spacing in a CD direction, the CD direction intersecting the direction of transport and the thickness direction;

a joining-portion forming step of forming a plurality of joining portions spacing in the direction of transport and the CD direction, the joining portions joining the pair of facing surfaces of the first sheet-like-member continuous body to each other, the joining-portion forming step including forming the plurality of joining portions on two sides of the elastic-member continuous bodies in the CD direction while maintaining the elastic-member continuous bodies in a state of being stretched in the direction of transport, the joining portions being formed so that, by direction-of-transport contraction and CD-direction expansion of the elastic member after a cutting step, the elastic member is sandwiched and pressed in the CD direction by the joining portions on the two sides, being attached to the first sheet-like member, the joining portions being formed so that a portion of at least one of the joining portions is overlapped with at least a portion of the side-seal section in a view of the first sheet-like-member continuous body in the thickness direction;

an overlaying step of overlaying, in the thickness direction, a second sheet-like-member continuous body on the first sheet-like-member continuous body in which the joining portions have been formed, the second sheet-like-member continuous body being continuous in the direction of transport;

a side-seal-section forming step of forming the side-seal section on each of two sides of each of cutting target positions in the direction of transport, the cutting target positions being set at a predetermined pitch in the direction of transport, the first sheet-like-member continuous body and the second sheet-like-member continuous body that have been overlaid on each other in the thickness direction being welded together in the side-seal section; and the cutting step of producing the absorbent article that has the elastic member, the first sheet-like member, and the second sheet-like member, the cutting step being performed after the side-seal-section forming step and by cutting the first sheet-like-member continuous body, the elastic-member continuous bodies, and the second sheet-like-member continuous body at each of the cutting target positions.

According to this method for manufacturing an absorbent article, the joining portions are formed so that a portion of at least one of the joining portions is overlapped with at least a portion of the side-seal section. Also, the elastic members are attached to the first sheet-like member by being sandwiched and pressed between the joining portions. Accordingly, it is possible to suppress the case where a portion not having stretchability is formed in a region of the first sheet-like member that is inward of the side-seal sections in the lateral direction, which is the direction of transport.

In such a method for manufacturing an absorbent article, at least one of the plurality of joining portions is provided at a position between the side-seal section and the cutting target position in the direction of transport.

According to this method for manufacturing an absorbent article, at least joining portion is provided at the position between the side-seal section and the cutting target position in the direction of transport. Accordingly, the elastic member is attached to the first sheet-like member by being sandwiched and pressed between not only the above-described overlapping-joining portions, but also the aforementioned joining portion. This makes it possible to more reliably suppress the case where a portion not having stretchability is formed in a region of the first sheet-like member that is inward of the side-seal sections in the lateral direction, which is the direction of transport.

In such a method for manufacturing an absorbent article, when the at least one joining portion that is overlapped with the side-seal section is defined as an overlapping-joining portion, at least one of the joining portions other than the overlapping-joining portion is provided straddling the cutting target position in the direction of transport.

According to this method for manufacturing an absorbent article, at least one of the joining portions is provided straddling the cutting target position in the direction of transport. Accordingly, the elastic member is attached to the first sheet-like member by being sandwiched and pressed between not only the above-described overlapping-joining portions, but also the aforementioned joining portion. This makes it possible to more reliably suppress the case where a portion not having stretchability is formed in a region of the first sheet-like member that is inward of the side-seal sections in the lateral direction, which is the direction of transport.

In such a method for manufacturing an absorbent article, the joining portions are provided for each of the elastic-member continuous bodies, and that at least one of the plurality of elastic-member continuous bodies and the joining portions provided for the at least one elastic-member continuous body are provided on a one side in the CD direction with respect to a portion of the side-seal section that is farthest located on the one side in the CD direction.

According to this method for manufacturing an absorbent article, the joining portions provided in correspondence with the at least one elastic-member continuous body are provided on the one side in the CD direction with respect to the portion of the side-seal section that is farthest located on the one side in the CD direction. Accordingly, it is possible to suppress the case where a large portion in which the pair of facing surfaces of the first sheet-like member are not joined to each other is formed in a CD-direction end portion. Accordingly, it is possible to suppress a separation of the pair of facing surfaces over a wide range due to such an unjoined portion.

In such a method for manufacturing an absorbent article, when the joining portion provided on the one side in the CD direction with respect to the portion of the side-seal section that is farthest located on the one side in the CD direction is defined as a one-side joining portion, of the first sheet-like member, a portion in which the one-side joining portion is provided is a portion that protrudes to the one side in the CD direction with respect to the second sheet-like member.

According to this method for manufacturing an absorbent article, the one-side joining portion is provided in a portion of the first sheet-like member that protrudes to the one side in the CD direction with respect to the second sheet-like member. Accordingly, even in the portion of the first sheet-like member that protrudes in the CD direction, it is possible to suppress the case where a large portion in which the pair of facing surfaces are not joined to each other is formed. Accordingly, it is possible to suppress a separation of the pair of facing surfaces over a wide range due to such an unjoined portion.

In such a method for manufacturing an absorbent article, in the first sheet-like-member continuous body and the second sheet-like-member continuous body, an adhesive is not provided in a portion where the side-seal section is to be formed.

According to this method for manufacturing an absorbent article, the adhesive is not provided in the portion where the side-seal section is to be formed. Accordingly, it is possible to suppress a reduction in welding strength that can occur if the adhesive is provided in such portion, that is to say the a reduction in welding strength in the side-seal section caused by a component in the adhesive.

In such a method for manufacturing an absorbent article, that a second elastic member is attached to the second sheet-like member, that the second sheet-like member has been given stretchability in the lateral direction by the second elastic member, that the method further comprises:

a second arranging step of arranging a plurality of second elastic-member continuous bodies between a pair of mutually-opposing facing surfaces of the second sheet-like-member continuous body,
  the plurality of second elastic-member continuous bodies being continuous in the direction of transport,
  the plurality of second elastic-member continuous bodies being in a stretched state in the direction of transport and being placed side-by-side spacing in the CD direction; and
a second-joining-portion forming step of forming a plurality of second joining portions spacing in the direction of transport and the CD direction,
  the second joining portions joining the pair of facing surfaces of the second sheet-like-member continuous body to each other,
    the second-joining-portion forming step including forming the plurality of second joining portions on two sides of the second elastic-member continuous bodies in the CD direction while maintaining the second elastic-member continuous bodies in a state of being stretched in the direction of transport,
    the second joining portions being formed so that, by direction-of-transport contraction and CD-direction expansion of the second elastic member after the cutting step, the second elastic member is sandwiched and pressed in the CD direction by the second joining portions on the two sides, being attached to the second sheet-like member,
    the second joining portions being formed so that a portion of at least one of the second joining portions is overlapped with at least a portion of the side-seal section in a view of the second sheet-like-member continuous body in the thickness direction,
  that in the overlaying step,
  the second sheet-like-member continuous body in which the second joining portions have been formed is overlaid in the thickness direction on the first sheet-like-member continuous body in which the joining portions have been formed, and
  that in the cutting step,
  the absorbent article that has the elastic member, the first sheet-like member, the second elastic member, and the second sheet-like member is produced by cutting the first sheet-like-member continuous body, the elastic-member continuous bodies, the second sheet-like-member continuous body, and the second elastic-member continuous bodies at each of the cutting target positions.

According to this method for manufacturing an absorbent article, the second elastic member and the second joining portions are provided in the second sheet-like member. Accordingly, stretchability in the lateral direction can be given to not only the first sheet-like member but also the second sheet-like member.

Also, the joining portions are formed so that a portion of at least one of the second joining portions is overlapped with the side-seal section. Also, the elastic members are attached to the second sheet-like member by being sandwiched and pressed between the second joining portions. Accordingly, it is possible to suppress the case where a portion not having stretchability is formed in a region of the second sheet-like member that is inward of the side-seal sections in the lateral direction, which is the direction of transport.

In such a method for manufacturing an absorbent article, when the joining portion that is in the first sheet-like-member continuous body and that is overlapped with at least a portion of the side-seal section is defined as a first overlapping-joining portion, and when the second joining portion that is in the second sheet-like-member continuous body and that is overlapped with at least a portion of the side-seal section is defined as a second overlapping-joining portion, in the overlaying step, the first sheet-like-member continuous body and the second sheet-like-member continuous body are overlaid such that at least one of a plurality of the first overlapping-joining portions is shifted in the direction of transport or the CD direction with respect to one of a plurality of the second overlapping-joining portions that is closest to the at least one first overlapping-joining portion.

According to this method for manufacturing an absorbent article, at least one of the plurality of first overlapping-joining portions is shifted in the direction of transport or the CD direction with respect to the second overlapping-joining portion that is closest in the CD direction to the at least one first overlapping-joining portion. Accordingly, it is possible to suppress a stiffness that can occur if the first overlapping-joining portion and the second overlapping-joining portion are completely overlapped, that is to say a stiffness of the side-seal section of the absorbent article will vary greatly, which is likely to cause the person touching that portion to feel discomfort.

In such a method for manufacturing an absorbent article, when the at least one joining portion that is overlapped with the side-seal section is defined as an overlapping-joining portion, and when a downstream one of the side-seal sections formed on two sides of each of the cutting target positions in the direction of transport is defined as a downstream side-seal section, the overlapping-joining portion is overlapped with the downstream side-seal section, and an upstream end of the overlapping-joining portion in the direction of transport is located downstream in the direction of transport with respect to an upstream end of the downstream side-seal section in the direction of transport.

According to this method for manufacturing an absorbent article, the upstream end of the overlapping-joining portion in the direction of transport is located downstream with respect to the upstream end of the downstream side-seal section in the direction of transport. Accordingly, after cutting is performed at the cutting target position, an end portion of the elastic member moves downstream in the direction of transport due to direction-of-transport contraction of the elastic member, and it is possible to suppress the case where the end portion of the elastic string protrudes upstream, in the direction of transport, of the downstream side-seal section. This therefore makes it possible to achieve a favorable appearance for the downstream side-seal section.

In such a method for manufacturing an absorbent article, the upstream end of the overlapping-joining portion in the direction of transport is located downstream in the direction of transport with respect to a central position of the downstream side-seal section in the direction of transport.

According to this method for manufacturing an absorbent article, the upstream end of the overlapping-joining portion in the direction of transport is located downstream with respect to the central position of the downstream side-seal section in the direction of transport. Accordingly, after cutting is performed at the cutting target position, an end portion of the elastic member moves downstream in the direction of transport due to direction-of-transport contraction of the elastic member, and it is possible to suppress the case where the end portion of the elastic string protrudes upstream, in the direction of transport, of the downstream side-seal section. This therefore makes it possible to achieve a favorable appearance for the downstream side-seal section.

In such a method for manufacturing an absorbent article, at least several of the joining portions are provided at a predetermined formation pitch in the direction of transport so as to span and extend beyond the side-seal section and the cutting target position in the direction of transport, and a size of the formation pitch is smaller than a direction-of-transport size of the side-seal section.

According to this method for manufacturing an absorbent article, the size of the formation pitch of the joining portions is smaller than the direction-of-transport size of the side-seal section. Accordingly, at least one of the joining portions can be overlapped with the side-seal section.

Further, a device for manufacturing an absorbent article, the absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, the thickness direction being a direction that intersects the lateral direction, the device including:

an arranging device configured to arrange a plurality of elastic-member continuous bodies between a pair of mutually-opposing facing surfaces of a first sheet-like-member continuous body that is being transported, a direction of transport of the first sheet-like-member continuous body conforming to the lateral direction, the plurality of elastic-member continuous bodies being continuous in the direction of transport, the first sheet-like-member continuous body being continuous in the direction of transport, the plurality of elastic-member continuous bodies being in a stretched state in the direction of transport and being placed side-by-side spacing in a CD direction, the CD direction intersecting the direction of transport and the thickness direction;

a joining-portion forming device configured to form a plurality of joining portions spacing in the direction of transport and the CD direction, the joining portions joining the pair of facing surfaces of the first sheet-like-member continuous body to each other, the joining-portion forming device forming the plurality of joining portions on two sides of the elastic-member continuous bodies in the CD direction while maintaining the elastic-member continuous bodies in a state of being stretched in the direction of transport, the forming is performed so that, by direction-of-transport contraction and CD-direction expansion of the elastic member at a position downstream the direction of transport with respect to a cutting device, the elastic member is sandwiched and pressed in the CD direction by the joining portions on the two sides, being attached to the first sheet-like member, the forming is performed so that a portion of at least one of the joining portions is overlapped with at least a portion of the side-seal section in a view of the first sheet-like-member continuous body in the thickness direction;

an overlaying device configured to overlay, in the thickness direction, a second sheet-like-member continuous body on the first sheet-like-member continuous body in which the joining portions have been formed, the second sheet-like-member continuous body being continuous in the direction of transport;

a side-seal-section forming device configured to form the side-seal section on each of two sides of each of cutting target positions in the direction of transport, the cutting target positions being set at a predetermined pitch in the direction of transport, the first sheet-like-member continuous body and the second sheet-like-member continuous body that have been overlaid on each other in the thickness direction being welded together in the side-seal section; and the cutting device configured to produce the absorbent article that has the elastic member, the first sheet-like member, and the second sheet-like member, at a position downstream in the direction of transport with respect to the side-seal-section forming device, the cutting device cutting the first sheet-like-member continuous body, the elastic-member continuous bodies, and the second sheet-like-member continuous body at each of the cutting target positions.

According to this device for manufacturing an absorbent article, it is possible to achieve actions and effects similar to those in the case of the manufacturing method described above.

Further, an absorbent article having a lateral direction, a vertical direction, and a front-rear direction that are orthogonal to each other, the absorbent article including:

a first sheet-like member;

a second sheet-like member;

a plurality of elastic members that are inserted along the lateral direction between a pair of mutually-opposing facing surfaces of the first sheet-like member, and that are arranged spacing in the vertical direction;

a plurality of joining portions that are for joining together the pair of facing surfaces and that are arranged with spacing in the lateral direction and in the vertical direction, the joining portions being formed on two sides of the elastic members in the vertical direction so that the elastic members are sandwiched and pressed between the joining portions on the two sides; and a side-seal section that is provided in each lateral end portion, a portion of at least one of the joining portions being overlapped with at least a portion of the side-seal section in a view of the first sheet-like member in the front-rear direction the first sheet-like member and the second sheet-like member being overlaid in the front-rear direction and welded in the side-seal section.

According to this absorbent article, the joining portions are formed so that a portion of at least one of the joining portions is overlapped with at least a portion of the side-seal section. Also, the elastic members are attached to the first sheet-like member by being sandwiched and pressed between the joining portions. Accordingly, it is possible to suppress the case where a portion not having stretchability is formed in a region of the first sheet-like member that is inward of the side-seal sections in the lateral direction, which is the direction of transport.

Figure 2:
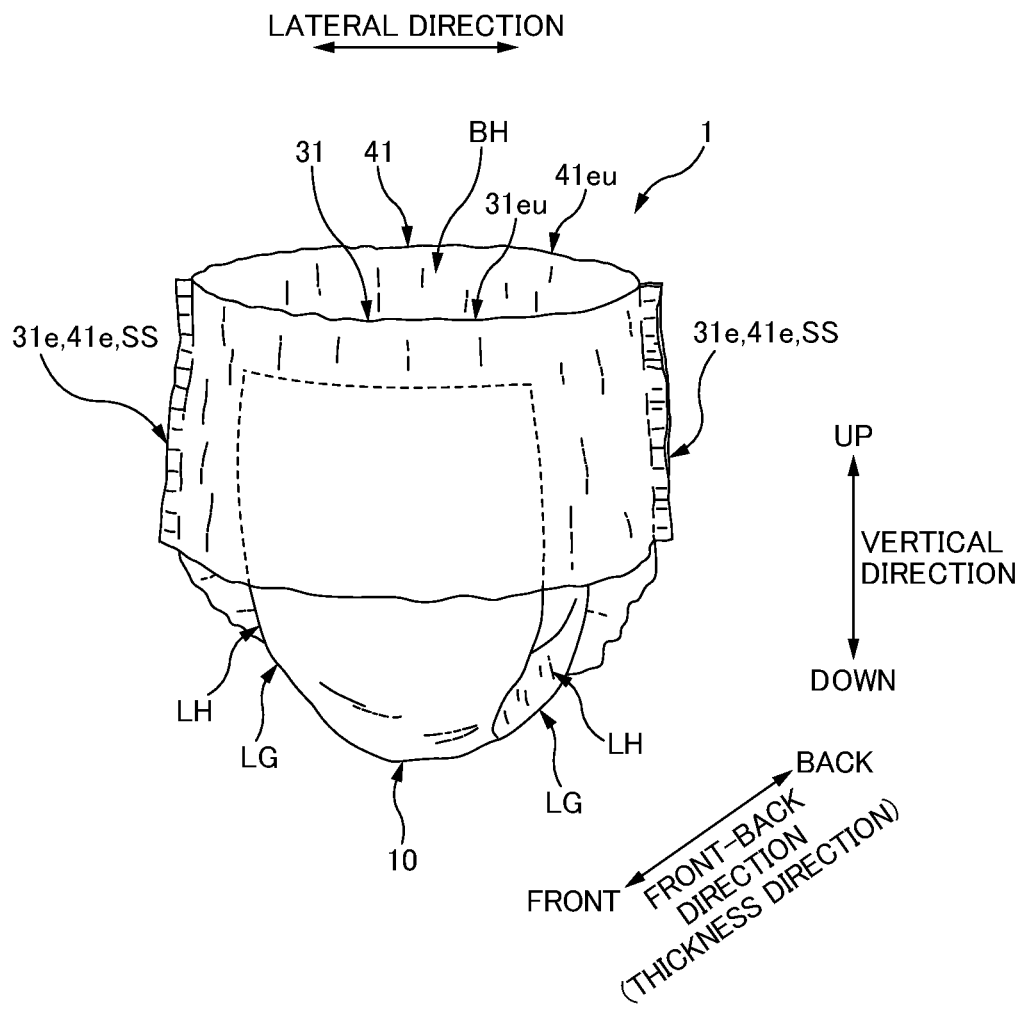
FIG. 2 is a schematic perspective view of a three piece-type of diaper 1 as one example of an absorbent article of one or more embodiments.

A method and a device for manufacturing an absorbent article according to one or more embodiments of the present invention are used in, for example, a manufacturing line for a disposable diaper 1 that is one example of an absorbent article. FIG. 2 is a schematic perspective view of a three piece-type of diaper 1 as one example of the diaper 1.

In the underpants-shaped state before being worn as shown in FIG. 2, the diaper 1 has a vertical direction, a lateral direction that is orthogonal to the vertical direction, and a "front-back direction" that is orthogonal to the vertical direction and the lateral direction. The vertical direction often conforms to the up-down direction when the diaper 1 is worn. For this reason, hereinafter, the vertical direction will also be called the up-down direction.

Note that with respect to the up-down direction, the upper side corresponds to the waist side of the wearer, and the lower side corresponds to the crotch side of the wearer. Also, with respect to the front-back direction, the front side corresponds to the stomach side of the wearer, and the back side corresponds to the back side of the wearer. Furthermore, with respect to the lateral direction, one side corresponds to the left side of the wearer, and the other side corresponds to the right side of the wearer.

In the underpants-shaped state shown in FIG. 2, the diaper 1 includes: a front band member 31 that extends in the lateral direction; a back band member 41 that extends along the lateral direction, is located on the back side of the front band member 31, and is for forming a waist opening BH on the upper side in the vertical direction along with the front band member 31; and an absorbent main body 10 that is a crotch portion provided between the front band member 31 and the back band member 41. The absorbent main body 10 is arranged at a position protruding farther downward in the vertical direction than the front band member 31 and the back band member 41 do.

Also, lateral end portions 31e of the front band member 31 and corresponding lateral end portions 41e of the back band member 41 are joined in side-seal sections SS. Accordingly, the front band member 31 and the back band member 41 respectively form leg openings LH on two lateral sides on the lower side along with the absorbent main body 10.

Figure 3:
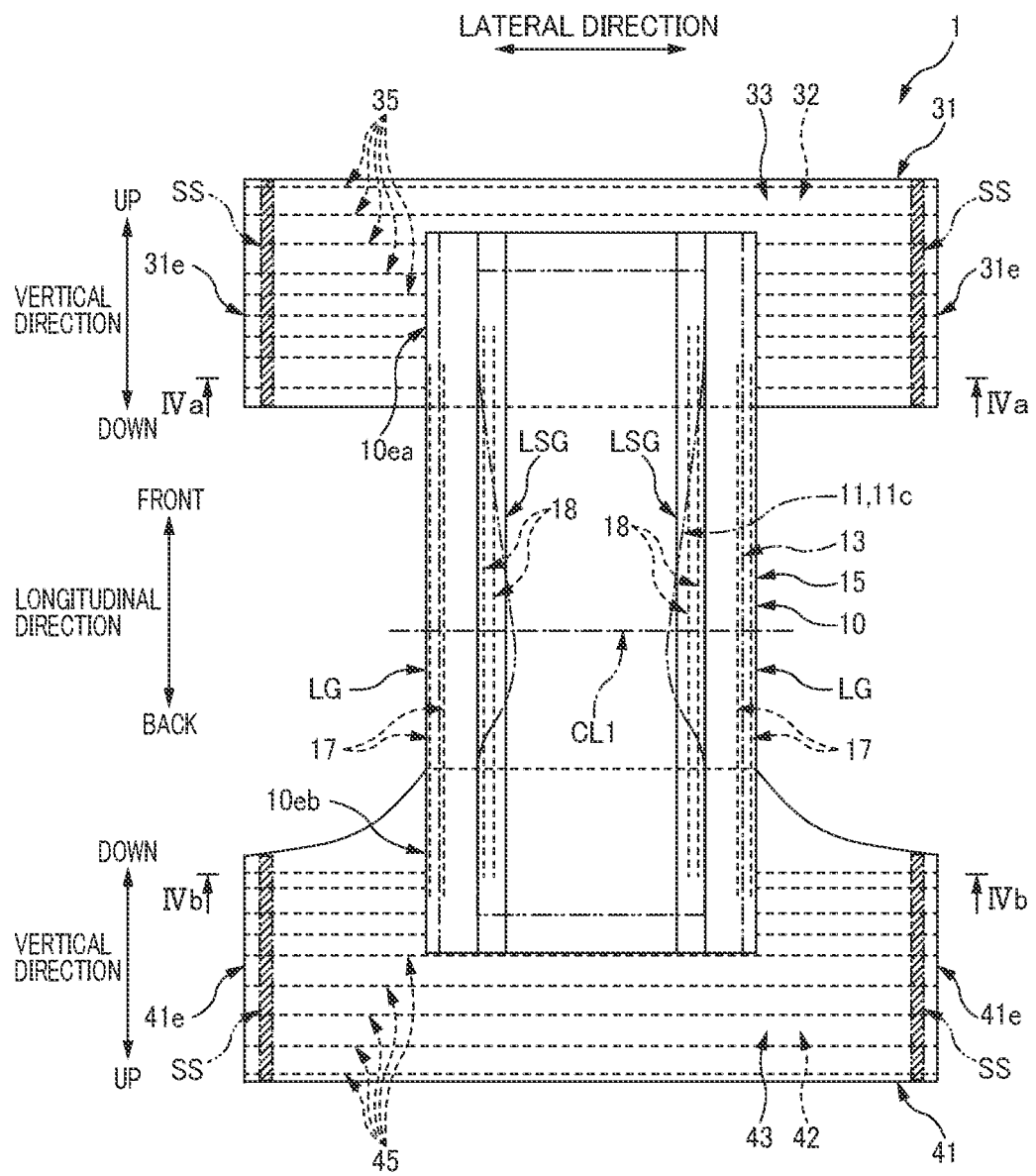
FIG. 3 is a schematic plan view of the diaper 1 in an unfolded state as viewed from a wearer's skin side.

FIG. 3 is a schematic plan view of the diaper 1 in an unfolded state as viewed from the wearer's skin side. Also, FIG. 4 includes a cross-sectional view along IVa-IVa and a cross-sectional view along IVb-IVb in FIG. 3.

Here, the unfolded state is a state in which the aforementioned side-seal sections SS on the two lateral sides of the diaper 1 in the underpants-shaped state shown in FIG. 2 are detached such that the front band member 31 and the back band member 41 separate from each other and the diaper 1 is opened in the vertical direction, and thus the diaper 1 is unfolded in a plan view.

Also, in this unfolded state, the diaper 1 is shown in a virtual state in which there is no stretchability in the members that constitute the diaper 1. For example, although the diaper 1 is provided with elastic members 17, 18, 35, and 45 for the purpose of giving stretchability to the diaper 1 in this example, in the aforementioned unfolded state, the diaper 1 is shown in a virtual state in which the elastic members 17, 18, 35, and 45 have no stretchability (contractive force) whatsoever.

In the unfolded state, the diaper 1 has a longitudinal direction, a lateral direction, and a thickness direction (direction passing through the paper plane in FIG. 3) as three directions that are orthogonal to each other. Note that the longitudinal direction conforms the previously described vertical direction. Also, with respect to the longitudinal direction, one side corresponds to the stomach side, and the other side corresponds to the back side. Also, the outer side in the longitudinal direction corresponds to the upper side in the vertical direction, and the inner side in the longitudinal direction corresponds to the lower side in the vertical direction. Given that the longitudinal direction and the vertical direction are directions that resemble each other in this way, for the sake of convenience hereinafter, the vertical direction will sometimes be used in place of the longitudinal direction in the unfolded state as well. Furthermore, the lateral direction is synonymous with the lateral direction in the previously described underpants-shaped state. Moreover, with respect to the thickness direction, one side corresponds to the skin side that comes into contact with the wearer's body, and the other side corresponds to the opposite non-skin side. Note that the thickness direction conforms to the previously described front-back direction.

In the unfolded state shown in FIG. 3, the front band member 31 is arranged extending in the lateral direction, and the back band member 41 is arranged extending in the lateral direction at a position that is separated from the front band member 31 by a predetermined gap in the longitudinal direction. The absorbent main body 10 spans along the longitudinal direction between the front band member 31 and the back band member 41, and longitudinal end portions 10ea and 10eb of the absorbent main body 10 are respectively joined and fixed to the closest band members 31 and 41, thus forming a substantially H-like outer shape in a plan view. The diaper 1 in this state is folded one time at a folding position that is at a predetermined longitudinal position CL1 of the absorbent main body 10 (a longitudinal central position CL1 of the diaper 1), and the lateral end portions 31e and 41e of the band members 31 and 41, which face each other in the folded state, are joined to each other in the previously described side-seal sections SS. Accordingly, the band members 31 and 41 become connected to each other in a ring shape, thus obtaining the diaper 1 in the underpants-shaped state in which the waist opening BH and the pair of leg openings LH are formed as shown in FIG. 2.

Figure 4:
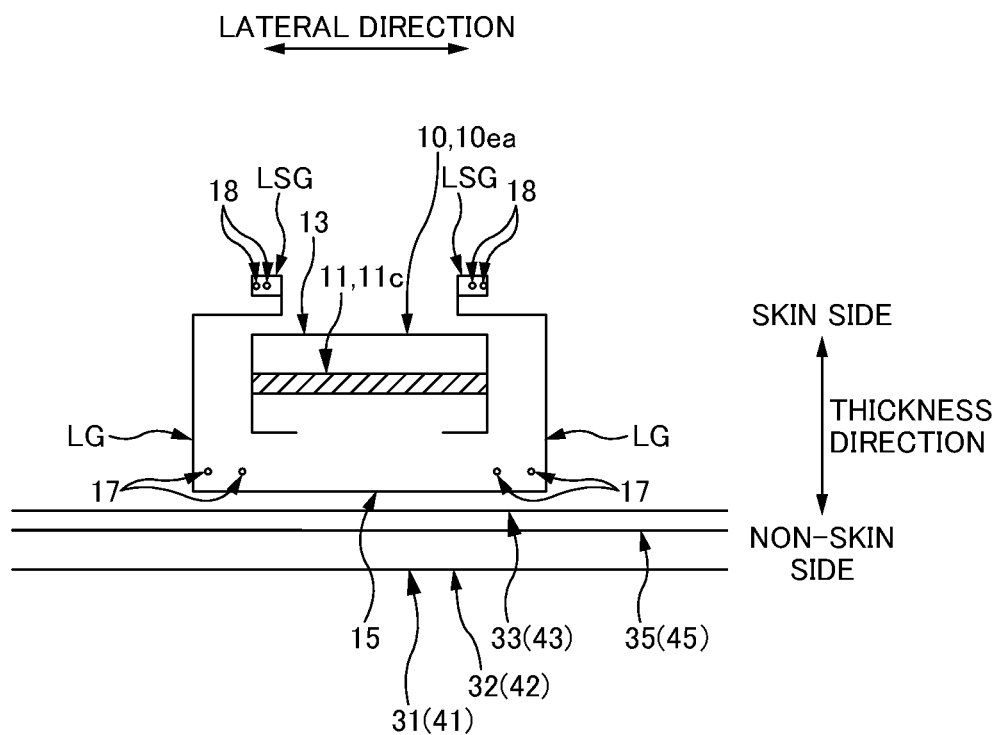
FIG. 4 includes a cross-sectional view along IVa-IVa and a cross-sectional view along IVb-IVb in FIG. 3.

The absorbent main body 10 has an approximately rectangular shape in a plan view in the unfolded state shown in FIG. 3. The longitudinal direction of the absorbent main body 10 conforms to the longitudinal direction of the diaper 1. Also, as shown in FIG. 4, the absorbent main body 10 includes: an absorbent body 11; a liquid-permeable top sheet 13 that covers the absorbent body 11 from the skin side and forms the skin-side surface of the absorbent main body 10; and a liquid-impermeable back sheet 15 that covers the absorbent body 11 from the non-skin side and forms the non-skin side of the absorbent main body 10.

The absorbent body 11 has a liquid-absorbent absorbent core 11c, and a core-wrapping sheet (not shown) that covers the outer circumferential surface of the core 11c. The absorbent core 11c is a molded body that is made of a predetermined liquid absorbent material such as pulp fiber or superabsorbent polymer, and is approximately hourglass-shaped in a plan view, as one example of a predetermined shape. The core-wrapping sheet can be made of a liquid-permeable sheet such as tissue paper or nonwoven fabric, but the core-wrapping sheet is not required to be provided. Also, the absorbent core 11c is not limited in any way to having the aforementioned approximately hourglass-like shape in a plan view, and may have another shape.

The top sheet 13 is a liquid-permeable soft sheet made of nonwoven fabric or the like. The back sheet 15 is also a liquid-impermeable soft sheet. One example of the back sheet 15 is a double-layer structure laminate sheet 15 including: a liquid-impermeable leak-proof sheet made of a polyethylene film (PE) or a polypropylene film; and an exterior sheet that is made of nonwoven fabric and is affixed to the non-skin side of the leak-proof sheet.

As shown in FIG. 3, at least the back sheet 15 is a sheet having a planar size according to which it projects from the absorbent body 11 in the longitudinal direction and the lateral direction. Leg gathers LG that stretch and contract in the longitudinal direction are formed in the portions that protrude in the lateral direction. Specifically, elastic strings 17 that serve as elastic members and extend in the longitudinal direction are fixed in the protruding portions in a state of being stretched in the longitudinal direction, thus forming the stretchable leg gathers LG in these portions.

Also, as shown in FIGS. 3 and 4, the absorbent main body 10 has barrier cuffs LSG as leak-proof wall portions in the lateral end portions for the purpose of preventing lateral leakage. Specifically, in the lateral end portions of the absorbent main body 10, a configurations are provided in which elastic strings 18 serving as elastic members 18 and extending in the longitudinal direction are attached, in a state of being stretched in the longitudinal direction, to sheet-like portions that will form the barrier cuffs LSG.

As shown in FIG. 3, the front band member 31 is a sheet-like member that is approximately rectangular in a plan view and is constituted by two nonwoven fabric sheets 32 and 33. Specifically, as shown in FIG. 4, the two nonwoven fabric sheets 32 and 33 are overlaid on each other in the thickness direction. And, the pair of facing surfaces that face each other are joined to each other by welded portions j (corresponding to joining portions) that are arranged discretely in the vertical direction (longitudinal direction) and the lateral direction as shown in later-described FIG. 5. As shown in FIG. 3, the front band member 31 is arranged so as to protrude out from the absorbent main body 10 on the two lateral sides, and is overlaid on and joined to the non-skin side of the front end portion 10ea of the absorbent main body 10.

Also, in this example, spunbond nonwoven fabric is used for both of the two nonwoven fabric sheets 32 and 33 pertaining to the front band member 31. Note that there is no limitation whatsoever to this, and it is possible to use various other types of nonwoven fabric such as SMS (spunbond/meltblown/spunbond) nonwoven fabric. Also, in this example, standalone fibers made of polypropylene (PP), which is a representative example of a thermoplastic, may be used as the constituent fibers of the nonwoven fabric, but there is no limitation whatsoever to this. For example, standalone fibers made of another thermoplastic resin such as polyethylene (PE) may be used, and composite fibers that have a sheath/core structure and are made of PE and PP or the like may be used. Note that the same also applies to the back band member 41 that will be described hereinafter.

Similarly to the front band member 31, the back band member 41 is also a sheet-like member that is approximately rectangular in a plan view and is constituted by two nonwoven fabric sheets 42 and 43. Specifically, as shown in FIG. 4, the two nonwoven fabric sheets 42 and 43 are overlaid on each other in the thickness direction, and, similarly to the front band member 31 shown in FIG. 5, the pair of facing surfaces that face each other are joined to each other by welded portions j (corresponding to second joining portions) that are arranged discretely in the vertical direction (longitudinal direction) and the lateral direction. As shown in FIG. 3, the back band member 41 is arranged so as to protrude out from the absorbent main body 10 on the two lateral sides, and is overlaid on and joined to the non-skin side of the back end portion 10eb of the absorbent main body 10.

Note that when the content described below is the same for both the front band member 31 and the back band member 41, only the front band member 31 will be described as a representative for both, and corresponding portions and the like of the back band member 41 are simply indicated in parentheses.

Figure 5:
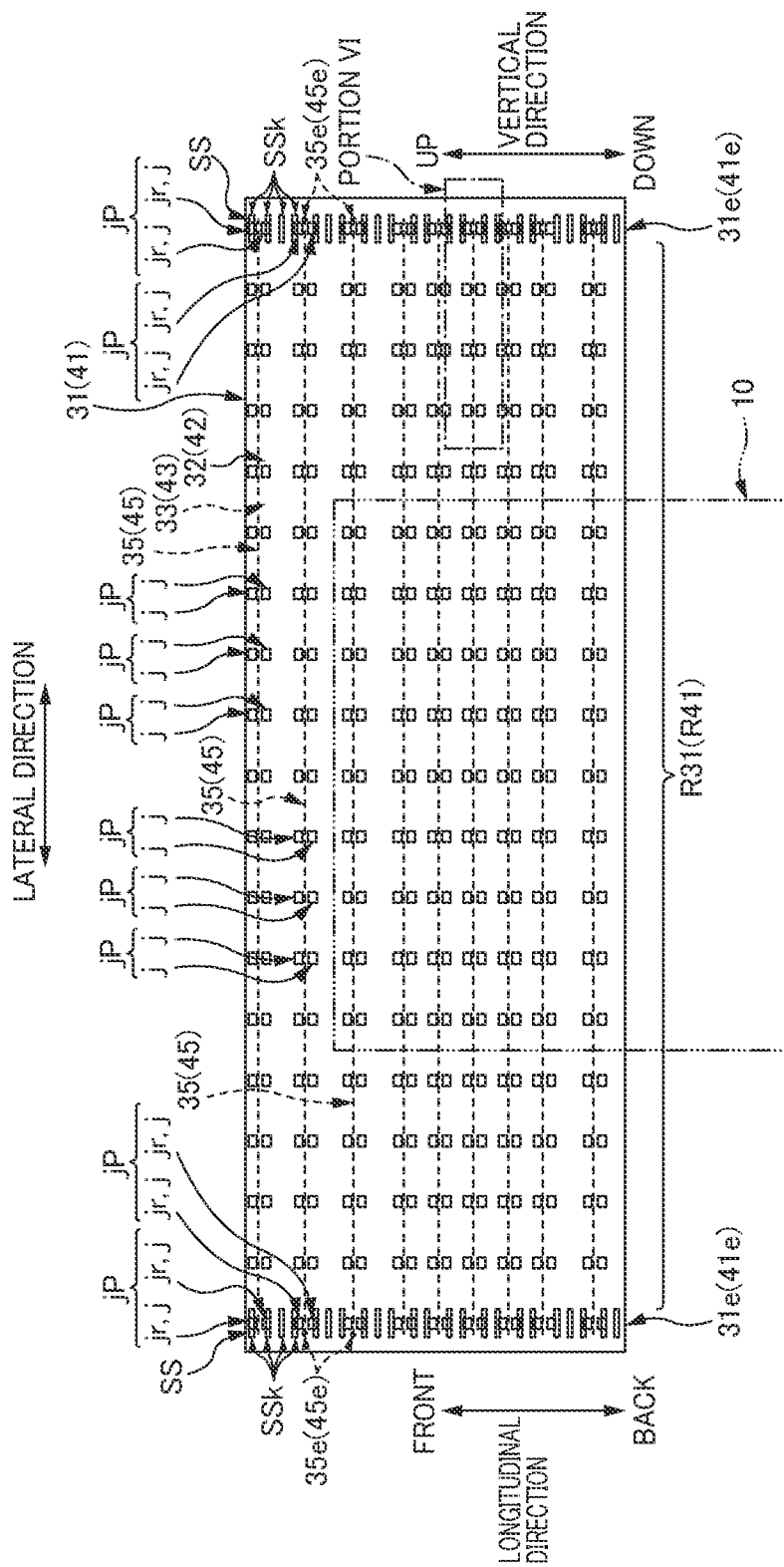
FIG. 5 is a schematic plan view of a front band member 31 in the unfolded state as viewed from the non-skin side.

FIG. 5 is a schematic plan view of the front band member 31 in the unfolded state as viewed from the non-skin side.

As shown in FIG. 5, the previously-described side-seal section SS is provided in each of the two end portions 31e (41e) in the lateral direction of the front band member 31 (41). In this example, the side-seal sections SS have welded portions SSk, SSk . . . that are the same shape as each other and are arranged side-by-side along a straight line that extends in the vertical direction. In the welded portions SSk, the nonwoven fabric sheet 33 of the front band member 31 and the nonwoven fabric sheet 43 of the back band member 41 are welded to each other, and a pair of mutually-opposing facing surfaces of the two nonwoven fabric sheets 32 and 33 pertaining to the front band member 31 are welded to each other, and furthermore, a pair of mutually-opposing facing surfaces of the two nonwoven fabric sheets 42 and 43 pertaining to the back band member 41 are welded to each other.

As shown in FIG. 5, a plurality of elastic strings 35, 35 . . . (45, 45 . . . ), which are elastic members (second elastic members) that extend in the lateral direction, are inserted side-by-side in the vertical direction between the pair of opposing facing surfaces of the two nonwoven fabric sheets 32 and 33 (42 and 43) of the front band member 31 (41). And the elastic strings 35, 35 . . . (45, 45 . . . ) are attached to the nonwoven fabric sheets 32 and 33 (42 and 43) with use of the welded portions j, j . . . that were mentioned above. Accordingly, the front band member 31 (41) is given stretchability in the lateral direction. Also, the previously mentioned welded portions j, j . . . not only have a function of joining the pair of facing surfaces of the two nonwoven fabrics 32 and 33 (42 and 43) to each other, but also have a function of attaching the elastic strings 35 (45) to the two nonwoven fabric sheets 32 and 33 (42 and 43).

FIGS. 6A and 6B are schematic enlarged views of a portion VI in FIG. 5, and are for illustrating the latter function of the welded portions j, that is to say the function of attaching the elastic strings 35 (45).

As shown in FIG. 5, the welded portions j, j . . . are provided for each of the elastic strings 35 (45) that extend in the lateral direction. Also, the welded portions j are formed in pairs of portions on respective sides of the corresponding elastic string 35 in the vertical direction, that is to say, each pair of welded portions j that are side-by-side in the vertical direction make up welded portion pair jP. These welded portion pairs jP are formed side-by-side in the lateral direction spacing between welded portion pairs jP that are adjacent in the lateral direction. Also, as shown in FIG. 6A, the pair of welded portions j that form each welded portion pair jP are separated by a gap Dj in the vertical direction, and the size of this gap Dj is set the same as or somewhat larger than a vertical size D35t (D45t) of the elastic strings 35 (45) in a state of being stretched to a target stretch factor in the lateral direction. In the diaper 1 in the underpants-shaped state shown in FIG. 2, the elastic strings 35 (45) are relaxed from the state of being stretched to the aforementioned stretch factor. Accordingly, in this underpants-shaped state, as shown in FIG. 6B, the elastic strings 35 (45) contract in the lateral direction and expand in the vertical direction, and here, based on the size relationship described above, the expansion of the elastic strings 35 (45) in the vertical direction is restricted by the pairs of welded portions j. Accordingly, the elastic strings 35 (45) are substantially sandwiched and pressed in the vertical direction by the pairs of welded portions j, and as a result, the elastic strings 35 (45) are attached in the front band member 31 (41).

It should be noted that the aforementioned stretch factor is a value R (=L1/L0) that indicates the ratio of a stretched total length L1 of the elastic string 35 (45) to a total length L0 in a natural no-load state. The aforementioned target stretch factor is selected from the range of 1.5 to 4.0, for example.

Also, as shown in FIGS. 5 and 6B, when the front band member 31 (41) is viewed in the thickness direction, a portion of at least one of the welded portions j, j . . . is overlapped with a welded portion SSk in the side-seal section SS (corresponding to a portion of the side-seal section). Hereinafter, this overlapping-welded portion j will also be called an "overlapping-welded portion jr (corresponding to an overlapping-joining portion)". As long as the overlapping-welded portion jr is provided, it is possible to suppress the following.

First, as shown in FIG. 5, the front band member 31 (41) includes a region R31 (R41) that is laterally inward of the welded portions SSk of the side-seal sections SS, and this region is a portion that comes into contact with the stomach side of the wearer's torso. For this reason, it is preferable that the inward region R31 (R41) has stretchability over the entire range in the lateral direction.

Figure 6:
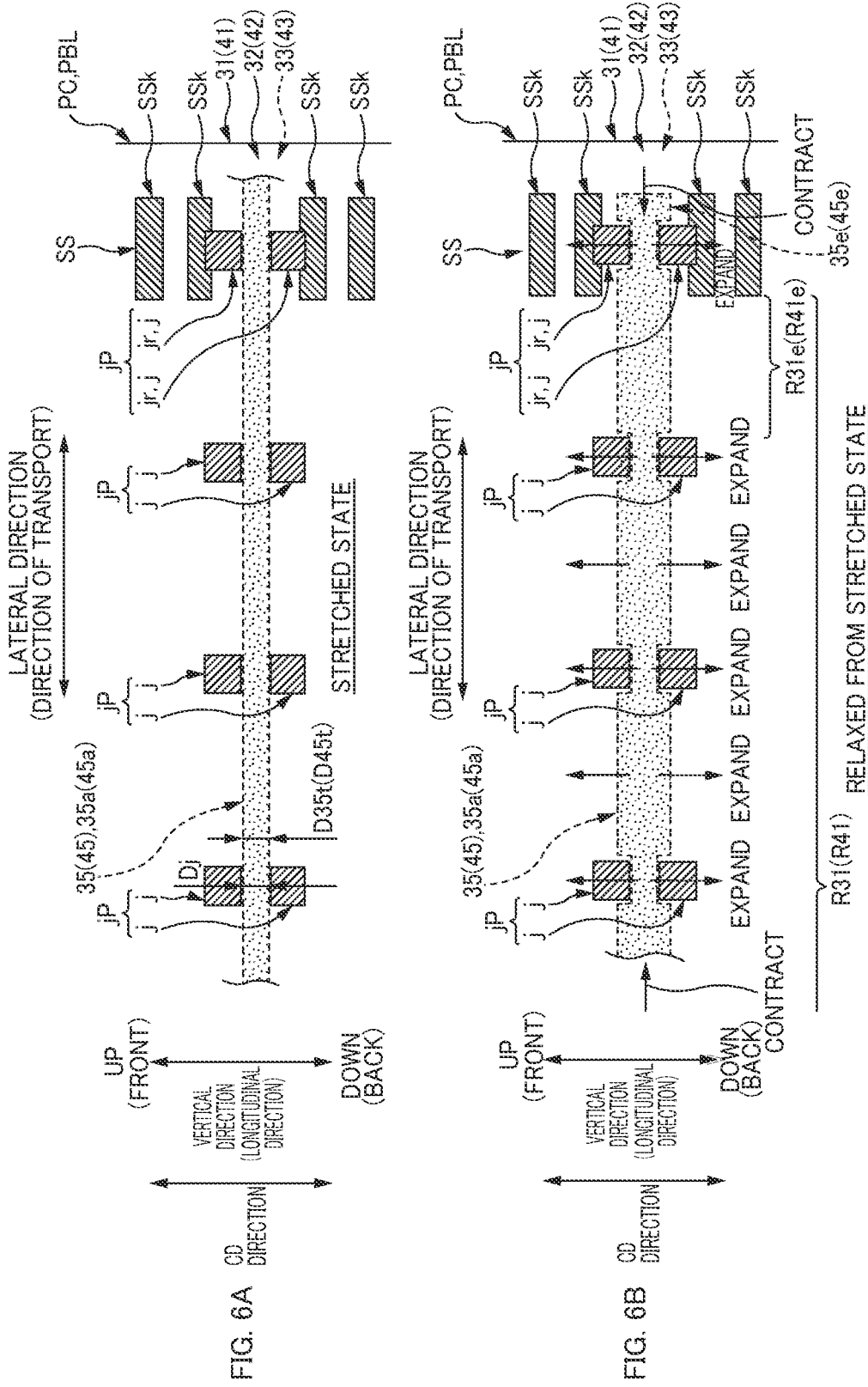
FIGS. 6A and 6B are illustrative views of an elastic string 35 (45) attachment function exhibited by welded portions j.
Figure 7:
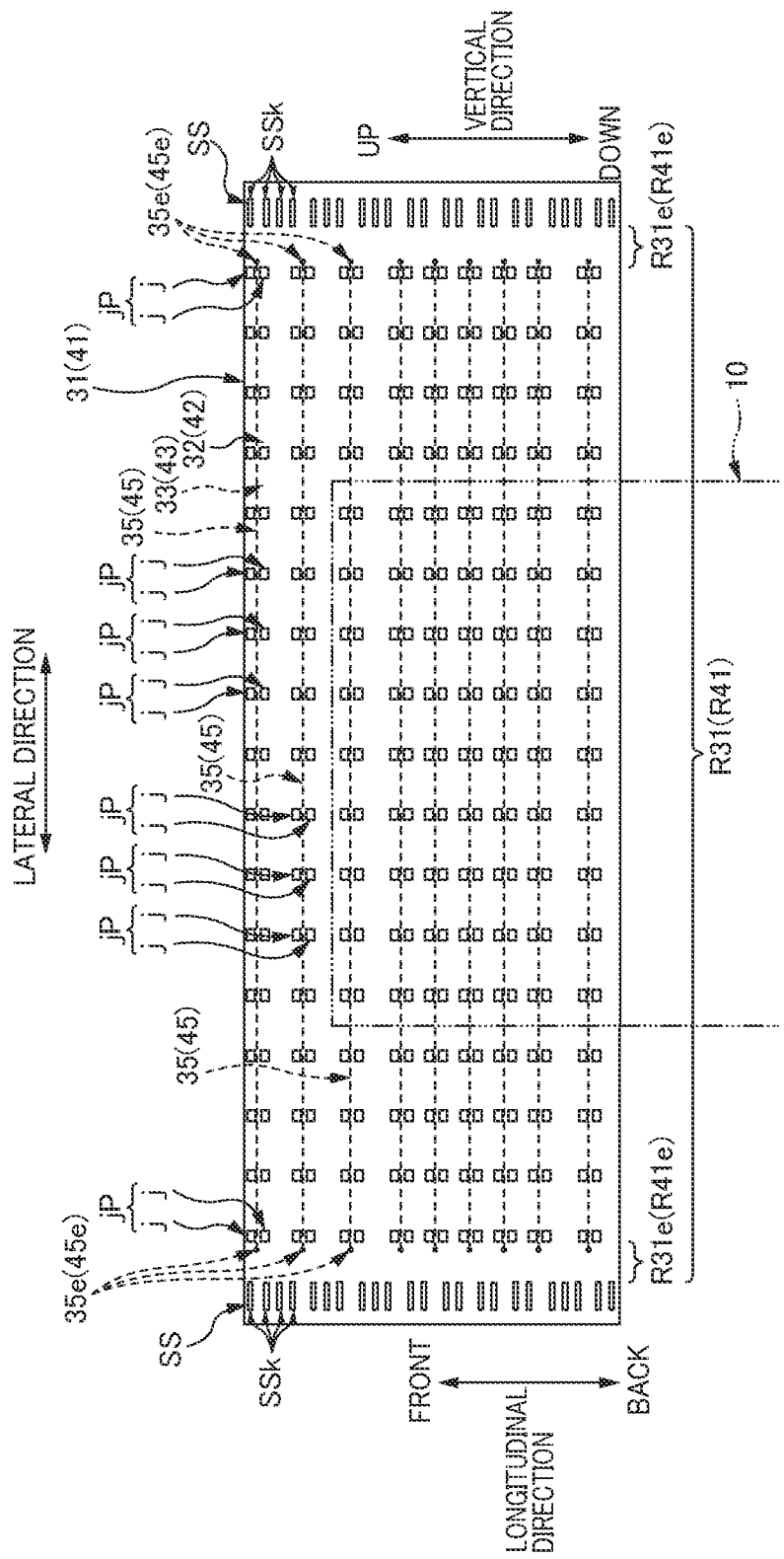
FIG. 7 is a schematic plan view of a front band member 31 (41) not having overlapping-welded portions jr as a comparative example, as viewed from the non-skin side.

Supposing that the above-described overlapping-welded portions jr are not provided as in a comparative example in FIG. 7. If the elastic strings 35 (45) contract in the lateral direction when the stretching is relaxed from the state in FIG. 6A to the state in FIG. 6B, there is a possibility that the lateral end portions 35e of the elastic strings 35 will move toward the inward region R31 (R41) in the front band member 31 (41) and enter the region R31 (R41) as shown in FIG. 7. Accordingly, the elastic strings 35 (45) disappear from lateral end portions R31e (R41e) of the inward region R31 (R41), and therefore the end portions R31e (R41e) no longer have stretchability.

However, in this respect, in the case where the overlapping-welded portions jr are provided as in the example in FIG. 5, when the stretched state of the elastic strings 35 (45) is relaxed from the state in FIG. 6A to the state in FIG. 6B, the end portions 35e (45e) of the elastic strings 35 (45) are prevented from moving to the inward region R31 (R41), due to the above-described sandwiching and pressing between the overlapping-welded portions at the positions of the welded portions SSk in the side-seal section SSk. Accordingly, it is possible to suppress the formation of portions that do not have stretchability in the inward region R31 (R41).

Note that although the overlapping-welded portion jr is provided for all of the elastic strings 35, 35 . . . (45, 45 . . . ) that are provided in the front band member 31 (41) in the example in FIG. 5, there is no limitation whatsoever to this. For example, concerning all of the elastic strings 35 (45) pertaining to the front band member 31 (41), as long as the overlapping-welded portion jr is provided for at least one of the elastic strings, one-third or more of the elastic strings, half or more of the elastic strings, or two-thirds or more of the elastic strings, it is possible to suppress the stretching of the elastic strings 35 (45) that are provided with the overlapping-welded portion jr. For this reason, elastic strings 35 (45) not provided with the overlapping-welded portion jr may exist among the elastic strings 35 (45) pertaining to the front band member 31 (41).

Figure 9A:
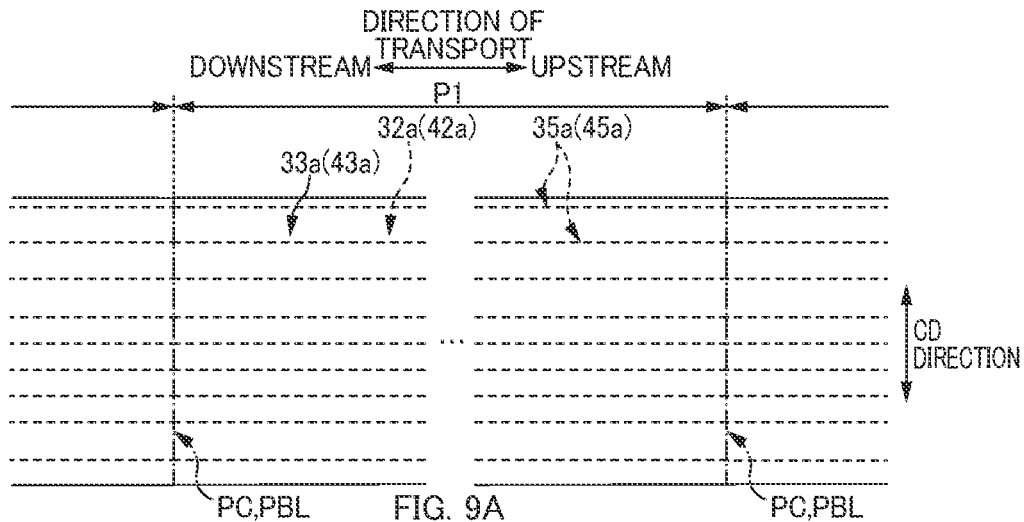
FIGS. 9A, 9B, and 9C are respectively schematic enlarged views of portions A, B, and C in FIG. 8.
Figure 9B:
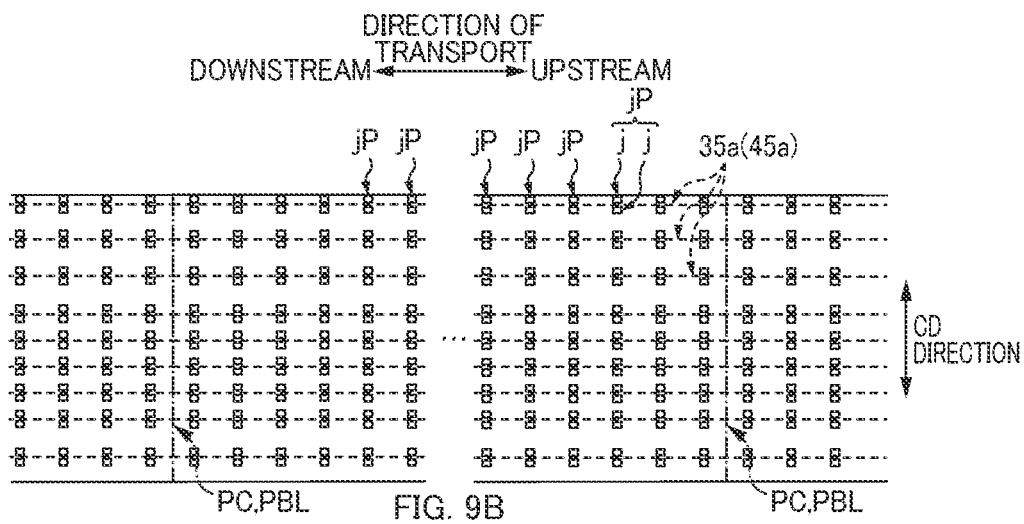
Figure 9C:
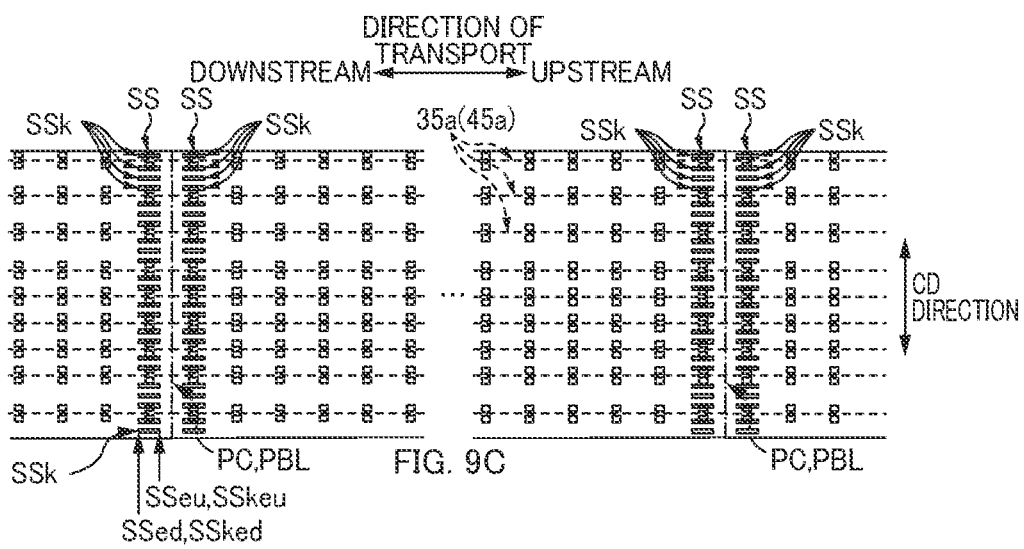

This diaper 1 is manufactured in a manufacturing line. FIG. 8 is a schematic plan view showing a partial perspective view of the manufacturing of the diaper 1 in the manufacturing line. Also, FIGS. 9A, 9B, and 9C are respectively schematic enlarged views of portions A, B, and C in FIG. 8. It should be noted that, more specifically, in FIG. 9C, the continuous sheets 42a and 43a pertaining to the back band member 41 would originally be visible instead of the continuous sheets 32a and 33a pertaining to the front band member 31, but for the sake of convenience in the description, it is assumed that the continuous sheets 32a and 33a pertaining to the front band member 31 are visible in the following description. Note that the same applies to later-described FIGS. 11A to 14 as well.

In this manufacturing line, for example, the two nonwoven fabric sheets 32 and 33 (corresponding to first sheet-like members) pertaining to the front band member 31 are transported in the form of continuous sheets 32a and 33a (corresponding to a first sheet-like-member continuous body) that are continuous in the direction of transport, and likewise, the two nonwoven fabric sheets 42 and 43 (corresponding to second sheet-like members) pertaining to the back band member 41 are transported in the form of continuous sheets 42a and 43a (corresponding to a second sheet-like-member continuous body) that are continuous in the direction of transport. The continuous sheets 32a, 33a, 42a, and 43a pass through processing positions PK1 to PK5 that are set in the direction of transport, and the continuous sheets 32a, 33a, 42a, and 43a are subjected to processing processes that correspond to the processing positions PK1, PK2, and so on.

Note that here, the direction that is orthogonal to both the thickness direction and the direction of transport of the continuous sheets 32a, 33a, 42a, and 43a is defined as "CD direction", and in this example, the continuous sheets 32a, 33a, 42a, and 43a (i.e., the two continuous sheets 32a and 33a pertaining to the front band member 31 and the two continuous sheets 42a and 43a pertaining to the back band member 41) are transported side-by-side in the CD direction. Note that there is no limitation whatsoever to this.

Also, in this example, the above-described processing positions, namely the first to fifth processing positions PK1 to PK5, are set side-by-side in this order from upstream to downstream in the direction of transport. At the processing positions PK1, PK2, and so on, the processes that are performed on the continuous sheets 32a and 33a pertaining to the front band member 31 are substantially the same as those performed on the two continuous sheets 42a and 43a pertaining to the back band member 41.

For this reason, the front band member 31 and the back band member 41 will not be distinguished from each other when the same content applies hereinafter. For example, in the following description, the term "band member 31 (41)" will simply be used, or the term "the two continuous sheets 32a and 33a (42a and 43a)" will simply be used. Note that in such cases, in the terms indicating the members, such as "the continuous sheets 32a and 33a (42a and 43a)", "the elastic strings 35 (45)", and "the elastic-string continuous bodies 35a (45a)", the reference signs that immediately follow the terms are the reference signs pertaining to the front band member 31, and the subsequent reference signs in the parentheses are the reference signs pertaining to the back band member 41.

As shown in FIG. 8, the two continuous sheets 32a and 33a (42a and 43a) pertaining to the band member 31 (41) are transported in a so-called lateral flow. Specifically, the two continuous sheets 32a and 33a (42a and 43a) are transported such that the direction corresponding to the lateral direction of the diaper 1 conforms to the direction of transport. For this reason, in the two continuous sheets 32a and 33a (42a and 43a), boundary positions PBL between two diapers 1 that are adjacent in the lateral direction are virtually set at a product pitch P1 in the direction of transport. Also, at the fifth processing position PK5 located at the end of the manufacturing line, the boundary position PBL is a cutting target position PC at which the two continuous sheets 32a and 33a (42a and 43a) are cut to produce a single-cut diaper 1.

Note that the two continuous sheets 32a and 33a (42a and 43a) pertaining to the band member 31 (41) are transported by appropriate transporting devices (not shown) such as a belt conveyor and transporting rollers. Accordingly, unless particularly stated otherwise, it is assumed that the two continuous sheets 32a and 33a (42a and 43a) are transported in the direction of transport by such transporting devices. Examples of the belt conveyor includes a normal belt conveyor that has an endless belt that is driven to rotate as a transporting surface, and a suction belt conveyor that has a function for suction to the outer circumferential surface of an endless belt.

Also, in this example, the stretchability of the continuous sheets 32a, 33a, 42a, and 43a is much smaller than the stretchability of the elastic strings 35 and 45, to the extent that such stretchability can be ignored. The continuous sheets 32a, 33a, 42a, and 43a are then transported from the first processing position PK1 to the fifth processing position PK5 while being stretched in the direction of transport.

The following is a detailed description of the diaper 1 manufacturing process.

As shown in FIG. 8, first, the two continuous sheets 32a and 33a (42a and 43a) pertaining to the band member 31 (41) pass the first processing position PK1. While passing, as shown in FIGS. 8 and 9A, the two continuous sheets 32a and 33a (42a and 43a) are overlaid on each other in the thickness direction. At this time, the elastic-string continuous bodies 35a, 35a . . . (45a, 45a . . . ), which are elastic-member continuous bodies (second elastic-member continuous bodies) and are continuous in the direction of transport, are inserted and arranged side-by-side in the CD direction between the two mutually-opposing facing surfaces of the two continuous sheets 32a and 33a (42a and 43a), in a state of being stretched to the previously described target stretch factor in the direction of transport (corresponding to an arranging step and a second arranging step).

Note that the elastic-string continuous bodies 35a (45a) are arranged on the pair of facing surfaces by a transporting device (corresponding to an arranging device) such as transporting rollers (not shown).

Also, at the same time as this overlaying or immediately thereafter, as shown in FIG. 9B, the previously described welded portions j, j . . . are formed as joining portions (second joining portions) in the two continuous sheets 32a and 33a (42a and 43a), and thus the pair of facing surfaces of the two continuous sheets 32a and 33a (42a and 43a) are joined to each other by the welded portions j, j . . . (corresponding to a joining-portion forming step and a second-joining-portion forming step).

Here, as previously described, in this manufacturing line, the lateral direction of the diaper 1 conforms to the direction of transport, and the vertical direction of the diaper 1 conforms to the CD direction. For this reason, the welded portions j are formed in pairs, on two sides in the CD direction of the elastic-string continuous bodies 35a (45a). Specifically, as shown in FIG. 9B, two welded portions j that are side-by-side on respective sides in the CD direction of each continuous body 35a (45a) form a welded portion pair jP. These welded portion pairs jP are formed side-by-side in the direction of transport spacing between welded portion pairs jP that are adjacent in the direction of transport.

Also, as shown in FIG. 6A, the two welded portions j that form each welded portion pair jP are separated by the gap Dj in the CD direction, and here, the size of the gap Dj is the same as or somewhat larger than the size D35t (D45t) in the CD direction of the elastic-string continuous bodies 35a (45a) which are located at the first processing position PK1 and which are in a state of being stretched to the target stretch factor in the direction of transport.

Accordingly, when the elastic-string continuous bodies 35a (45a) are cut at the later-described fifth processing position PK5 thus relaxing the stretched state of the elastic strings 35 (45), as shown in FIG. 6B, the elastic strings 35 (45) contract in the direction of transport and attempt to expand in the CD direction. But, the elastic strings 35 (45) are sandwiched and pressed in the CD direction between the pair of welded portions j, and thus the elastic strings 35 (45) are attached to the two nonwoven fabric sheets 32 and 33 (42 and 43) of the band member 31 (41).

Also, as can be understood from a comparison of FIGS. 9B and 9C, when the continuous sheets 32a and 33a (42a and 43a) are viewed in the thickness direction, a portion of at least one of the welded portions j, j . . . is overlapped with a welded portion SSk in the side-seal section SS that is to be formed thereafter. In other words, the previously-described overlapping-welded portion jr (j) is provided. Accordingly, when the elastic-string continuous bodies 35a, 35a . . . (45a, 45a . . . ) are cut at the cutting target position PC together with the two continuous sheets 32a and 33a (42a and 43a) at a time of being placed the later-described fifth processing position PK5, the end portions 35e (45e) of the relaxed elastic strings 35 (45) are sandwiched and pressed between pairs of the overlapping-welded portions jr (j). This makes it possible for these end portions 35e (45e) to be substantially stopped at the position of the side-seal section SS as shown in FIG. 5. As a result, it is possible to suppress the case where the end portions 35e (45e) enter the region R31 (R41) that is laterally inward of the welded portions SSk of the side-seal sections SS in the band members 31 (31).

Figure 10:
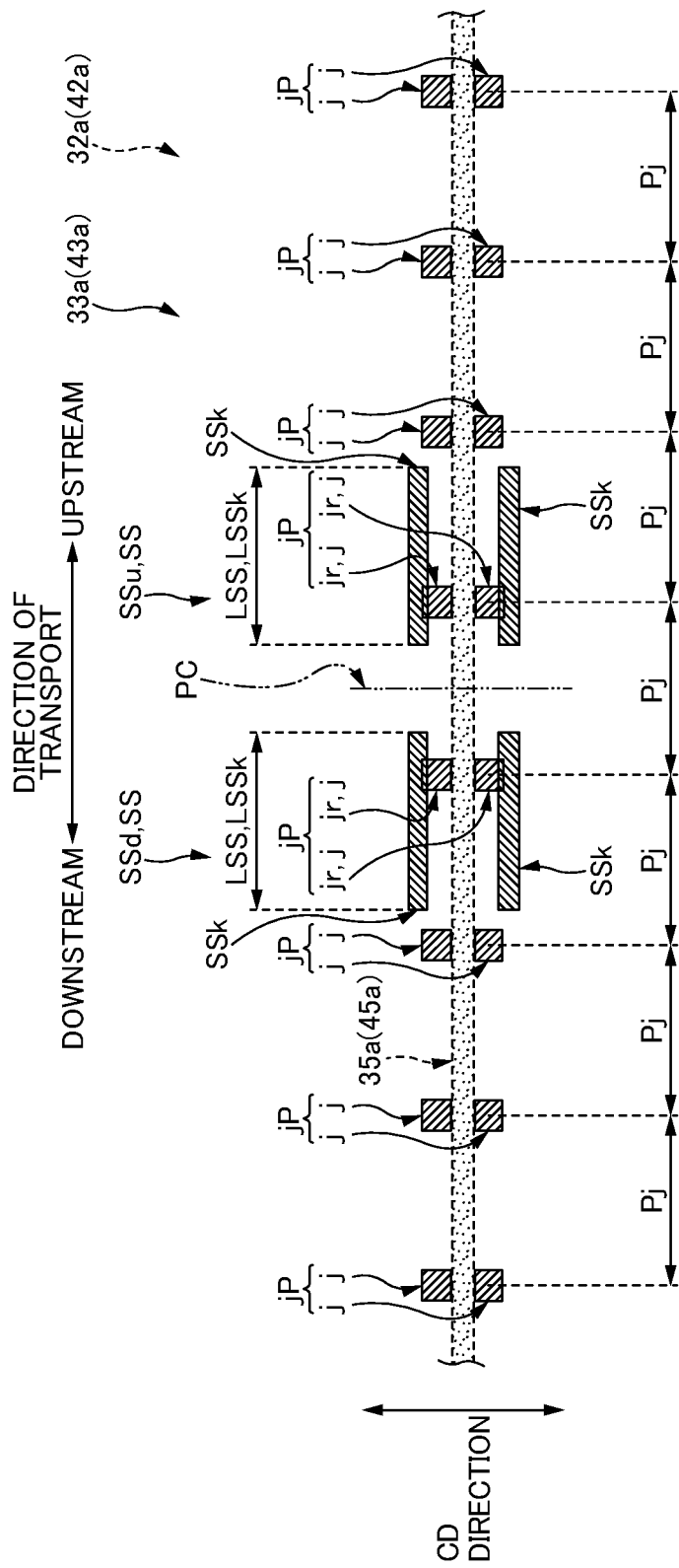
FIG. 10 is a schematic view showing an enlarged view of an example in which the size of a formation pitch Pj in the direction of transport of welded portions j, j . . . is set smaller than a size LSS in the direction of transport of a side-seal section SS.

Note that the overlapping-welded portions jr (j) are reliably provided by performing the following, for example. Specifically, as shown in FIG. 10, first, several welded portions j, j . . . are provided at a predetermined formation pitch Pj in the direction of transport so as to span and extend beyond the position of the side-seal section SS and the cutting target position PC in the direction of transport. In this example, the welded portions j, j . . . are provided at the formation pitch Pj over the entire length in the direction of transport. Also, when the size of the formation pitch Pj and the direction-of-transport size LSS of the side-seal section SS at a time of being placed at the fourth processing position PK4 are compared, the size of the former formation pitch Pj is smaller than the size LSS of the latter side-seal section SS. In this example, the size of the formation pitch Pj is smaller than a direction-of-transport size LSSk of the welded portions SSk of the side-seal section SS. According to this configuration, a portion of at least one welded portion j can be reliably overlapped with the side-seal section SS, or in other words, the overlapping-welded portion jr can be formed reliably.

It should be noted that in this example, as shown in FIG. 9C, the side-seal section SS is constituted by a plurality of welded portions SSk, SSk . . . that have the same shape and are side-by-side along one straight line that extends in the CD direction. The side-seal section SS has an end SSeu located upstream and an end SSed located downstream in the direction of transport, and the welded portions SSk has an end SSkeu located upstream and an end SSked located downstream in the direction of transport. The positions of the upstream and downstream ends SSeu and SSed of the side-seal section SS respectively match the positions of the upstream and downstream ends SSkeu and SSked of the welded portions SSk. Accordingly, the direction-of-transport size LSS of the side-seal section SS and the direction-of-transport size LSSk of the welded portion SSk are the same value as each other as shown in FIG. 10. Accordingly, the foregoing comparison with the formation pitch Pj can be performed with the size LSSk of the welded portion SSk instead of the size LSS of the side-seal section SS.

However, although not shown, if the side-seal section SS were to have a plurality of welded portions SSk, SSk . . . in the direction of transport, the above configuration would not be possible. Specifically, in this case, the upstream end SSkeu of the welded portion SSk located most upstream in the direction of transport in the side-seal section SS is the upstream end SSeu of the side-seal section SS, and the downstream end SSked in the welded portion SSk located most downstream in the direction of transport in the side-seal section SS is the downstream end SSed of the side-seal section SS. Accordingly, the size LSS of the side-seal section SS is the direction-of-transport distance between the upstream end SSkeu of the most upstream welded portion SSk and the downstream end SSked of the most downstream welded portion SSk. Also, in this case, the central position CSS in the direction of transport of the side-seal section SS refers to the midpoint between the upstream end SSkeu of the most upstream welded portion SSk and the downstream end SSked of the most downstream welded portion SSk. The upstream end SSeu, the downstream end SSed, and the central position CSS of this side-seal section SS are defined in a similar manner for cases that will be described later with reference to FIGS. 11A and 11B.

The welded portions j (including the overlapping-welded portions jr) can be formed using a heat sealing device or an ultrasonic sealing device (corresponding to a joining-portion forming device) that is not shown, for example. A heat sealing device has a pair of rolls that are heated while rotating in the direction of transport, for example. One of the rolls is a heat emboss roll that has protrusion portions corresponding to the welded portions j on the outer circumferential surface, and the other roll is an anvil roll that receives the protrusion portions with a smooth outer circumferential surface. Also, an ultrasonic sealing device has a horn that has a vibrating surface that vibrates in a normal direction, and an anvil roll that rotates in the direction of transport, for example. The anvil roll has protrusion portions that correspond to the welded portions j on the outer circumferential surface in order to receive the vibrating surface.

Next, as shown in FIG. 8, the two continuous sheets 32a and 33a pertaining to the front band member 31 and the two continuous sheets 42a and 43a pertaining to the back band member 41 all pass the second processing position PK2. At this time, the single-cut absorbent main body 10 produced in a separate step (not shown) is fixed in a state of spanning between the two continuous sheets 32a and 33a pertaining to the front band member 31 and the two continuous sheets 42a and 43a pertaining to the back band member 41, thus forming the approximately ladder-shaped diaper continuous body 1hs in which approximately H-shaped unfolded diapers 1h, 1h . . . are continuous with each other.

The absorbent main body 10 is fixed using a rotating drum device that is not shown, for example. The rotating drum device has a rotating drum that rotates in the direction of transport, and the rotating drum has a plurality of holding portions that detachably hold the absorbent main body 10 to the outer circumferential surface, for example.

Next, the approximately ladder-shaped diaper continuous body 1hs passes the third processing position PK3. At this time, the absorbent main body 10 is folded one time at a predetermined position CL1 in the CD direction, and therefore the two continuous sheets 32a and 33a pertaining to the front band member 31 and the two continuous sheets 42a and 43a pertaining to the back band member 41 are overlaid on each other in the thickness direction (corresponding to an overlaying step).

The folding can be performed using a fold guiding device (corresponding to an overlaying device) that is not shown, for example. The fold guiding device has a guide plate and guide rollers that are arranged at predetermined positions in the direction of transport, for example. The guide plate and the guide rollers guide the approximately ladder-shaped diaper continuous body 1hs passing at the arrangement position so as to be folded one time.

Next, the folded diaper continuous body 1hsb passes the fourth processing position PK4. At this time, concerning the two continuous sheets 32a and 33a pertaining to the front band member 31 and concerning the two continuous sheets 42a and 43a pertaining to the back band member 41, the continuous sheets 32a and 33a and 42a and 43a which are overlaid in the thickness direction are welded at positions on two sides of the cutting target position PC in the direction of transport so as to form a pair of side-seal sections SS (corresponding to a side-seal-section forming step), thus fixing the diaper continuous body 1hsb in the folded state. This consequently produces an underpants-shaped diaper continuous body is in which a plurality of underpants-shaped diapers 1, 1 . . . are connected in the lateral direction.

Here, given that the CD direction conforms to the vertical direction of the diaper 1, as shown in FIG. 9C, the side-seal sections SS have a plurality of welded portions SSk, SSk . . . that are side-by-side in the CD direction (vertical direction). The welded portions SSk weld together the continuous sheet 33a of the front band member 31 and the continuous sheet 43a of the back band member 41, weld together the pair of facing surfaces of the continuous sheets 32a and 33a of the front band member 31, and weld together the pair of facing surfaces of the continuous sheets 42a and 43a of the back band member 41 (FIG. 8).

Also, in this example in FIG. 9C, the planar shape of the welded portions SSk is a laterally elongated rectangular shape that is longer in the lateral direction, which is the CD direction, than in the vertical direction, which is the direction of transport. Note that there is no limitation whatsoever to this. For example, it may have a parallelogram shape or oval shape, or may have another shape. Also, in this example, the longitudinal direction of the welded portions SSk conforms to the lateral direction, which is the direction of transport, but there is no limitation whatsoever to this. In other words, the longitudinal direction of the welded portions SSk may conform to the vertical direction, which is the CD direction, or may conform to a direction that intersects both the lateral direction and the vertical direction.

It should be noted that in this example, in the for-front-band-member-31 continuous sheets 32a and 33a and the for-back-band-member-41 continuous sheets 42a and 43a, the adhesive is not provided in the portions where the side-seal sections SS are to be formed, that is to say the portions where the welded portions SSk, SSk . . . are to be formed. Accordingly, it is possible to suppress a reduction in welding strength that can occur if the adhesive is provided in such portions, that is to say a reduction in welding strength in the side-seal sections SS caused by a component in the adhesive.

The side-seal sections SS can be formed using a heat sealing device or an ultrasonic sealing device (corresponding to a side-seal-section forming device) that is not shown, for example. A heat sealing device has a pair of rolls that are heated while rotating in the direction of transport, for example. One of the rolls is a heat emboss roll that has protrusion portions corresponding to the welded portions SSk of the side-seal sections SS on the outer circumferential surface, and the other roll is an anvil roll that receives the protrusion portions with a smooth outer circumferential surface. Also, an ultrasonic sealing device has a horn that has a vibrating surface that vibrates in a normal direction, and an anvil roll that rotates in the direction of transport, for example. The anvil roll has protrusion portions that correspond to the welded portions SSk on the outer circumferential surface in order to receive the vibrating surface.

Next, as shown in FIG. 8, the underpants-shaped diaper continuous body is passes the fifth processing position PK5. At this time, the continuous body 1s is cut at the cutting target position PC that is located between a pair of side-seal sections SS (corresponding to a cutting step), thus obtaining the diaper 1.

Note that at the time of this cutting, the two continuous sheets 32a and 33a (42a and 43a) pertaining to the front band member 31 and the back band member 41 and the elastic-string continuous bodies 35a, 35a . . . (45a, 45a . . . ) are cut at the cutting target position PC. Due to the corresponding relaxation of the stretched state of the elastic strings 35 (45), the elastic strings 35 (45) are sandwiched and pressed by the pairs of welded portions j in the welded portion pairs jP and are thus attached to the band members 31 and 41, and this is the same as in the description of the first processing position PK1.

This cutting can be performed using a cutter device (corresponding to a cutting device) that is not shown, for example. A cutter device has a pair of rolls that rotate in the direction of transport, for example. One of the rolls is a cutter roll that has a cutter blade on the outer circumferential surface, and the other roll is an anvil roll having an outer circumferential surface that receives the cutter blade.

Figure 11A:
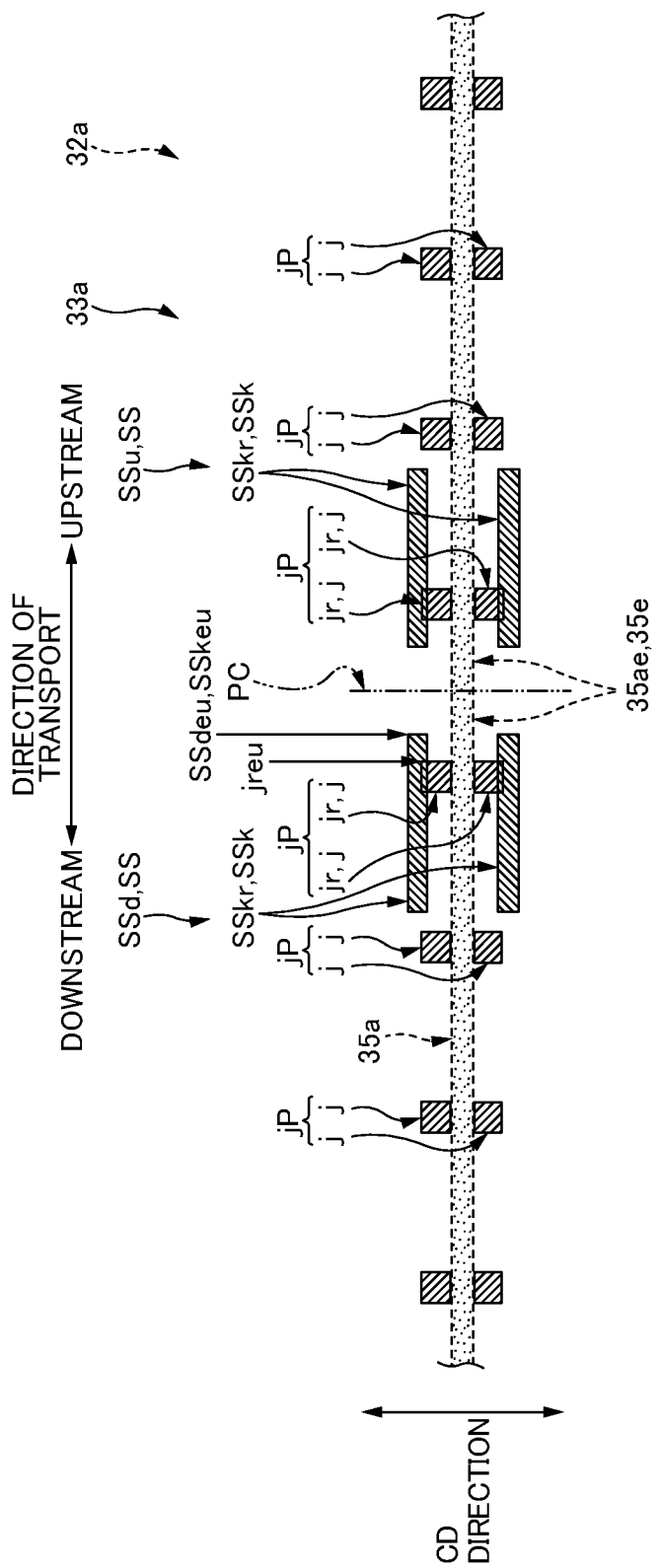
FIG. 11A is a schematic view for describing an example of a state where overlapping-welded portions jr and the side-seal section SS are overlapped.
Figure 11B:
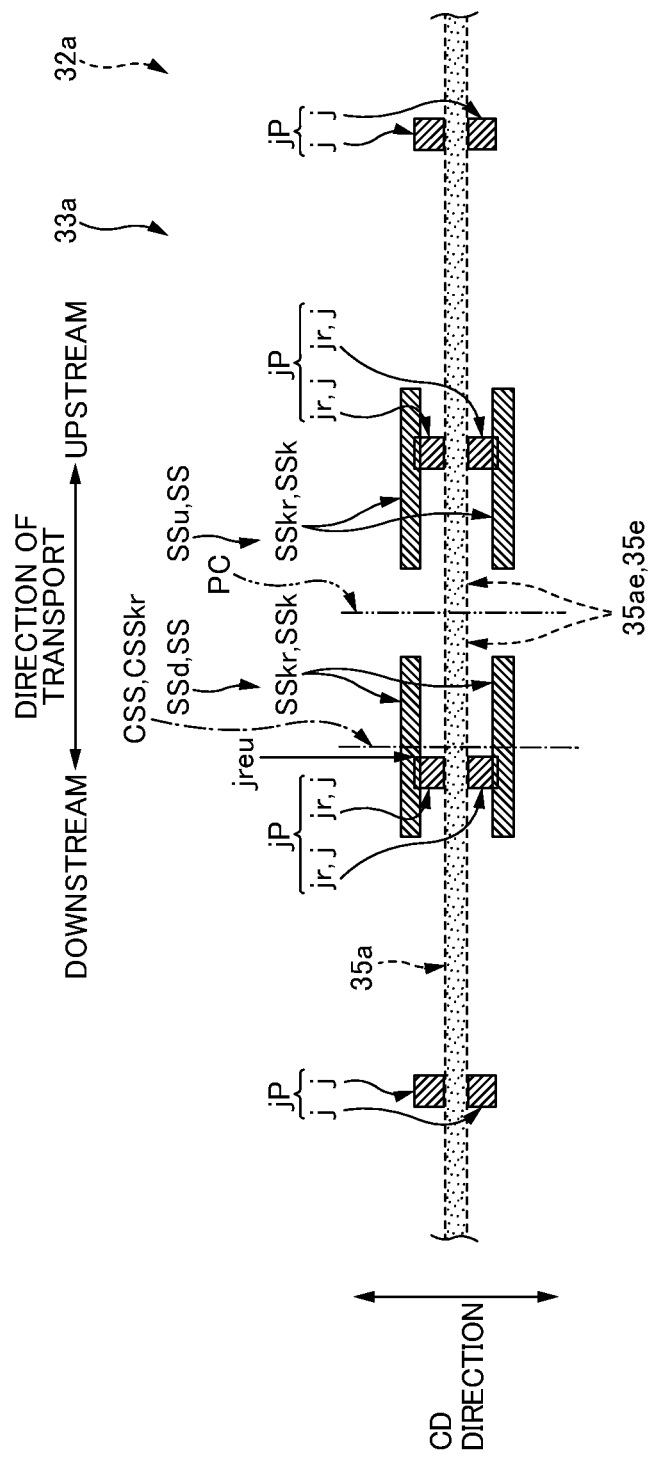
FIG. 11B is a schematic view of the same.

FIGS. 11A and 11B are schematic views for specifically describing an example of a state where overlapping-welded portions jr and the side-seal section SS are overlapped. Note that both of these figures are schematic plan views of a portion in the vicinity of the cutting target position PC in the underpants-shaped diaper continuous body is immediately before being cut at the fifth processing position PK5, as viewed in the thickness direction.

The content of the following description is the same for both the overlapping-welded portions jr that pertain to the front band member 31 and the overlapping-welded portions jr that pertain to the back band member 41. For this reason, only the former will be described as a representative for both, and descriptions will not be given for the latter.

As previously described with reference to FIGS. 6A and 6B, when the diaper continuous body 1s is cut at the cutting target position PC, the two end portions 35e are formed in each elastic string 35 on respective sides of the cutting target position PC in the direction of transport. Accordingly, as shown in FIG. 11A, the elastic-string continuous body 35a has portions 35ae that are to be the end portions 35e of the elastic string 35, and these portions 35ae are located on respective sides of the cutting target position PC in the direction of transport. Also, the overlapping-welded portions jr ultimately attach the end portions 35e to the pair of facing surfaces of the continuous sheets 32a and 33a. For this purpose, in both of the examples in FIGS. 11A and 11B, the overlapping-welded portions jr are formed on respective sides of the cutting target position PC in the direction of transport.

Note that the two overlapping-welded portions jr on the respective sides are formed so as to be approximately in line symmetry with each other with respect to the cutting target position PC. Similarly, the two side-seal sections SS formed on the respective sides of the cutting target position PC are formed so as to be approximately in line symmetry with each other with respect to the cutting target position PC. For this reason, only the overlapping-welded portion jr and the side-seal section SS that are located downstream in the direction of transport with respect to the cutting target position PC will be described hereinafter, and the overlapping-welded portion jr and the side-seal section SS that are located upstream will not be described.

Also, in the following description, out of the two side-seal sections SS that are formed on two sides in the direction of transport with respect to the cutting target position PC, the side-seal section SS located downstream in the direction of transport will also be referred to as a "downstream side-seal section SSd", and the side-seal section SS located upstream will also be referred to as an "upstream side-seal section SSu".

In the example in FIG. 11A, the welded portions j that are located closest to the cutting target position PC are overlapping-welded portions jr. Also, upstream ends jreu of the overlapping-welded portions jr in the direction of transport are located downstream in the direction of transport with respect to the upstream end SSdeu of the downstream side-seal section SSd in the direction of transport. More specifically, in this example, the overlapping-welded portions jr are located downstream in the direction of transport with respect to upstream ends SSkreu of welded portions SSkr which are the welded portions SSk, SSk . . . of the downstream side-seal section SSd and which are overlapped with the overlapping-welded portions jr.

Accordingly, after cutting is performed at the cutting target position PC, an end portion 35e of the elastic string 35 moves downstream in the direction of transport due to direction-of-transport contraction of the elastic string 35, and it is possible to suppress the case where the end portion 35e of the elastic string 35 protrudes upstream, in the direction of transport, of the position of the downstream side-seal section SSd. This therefore makes it possible to achieve a favorable appearance for the downstream side-seal section SSd.

Figure 12A:
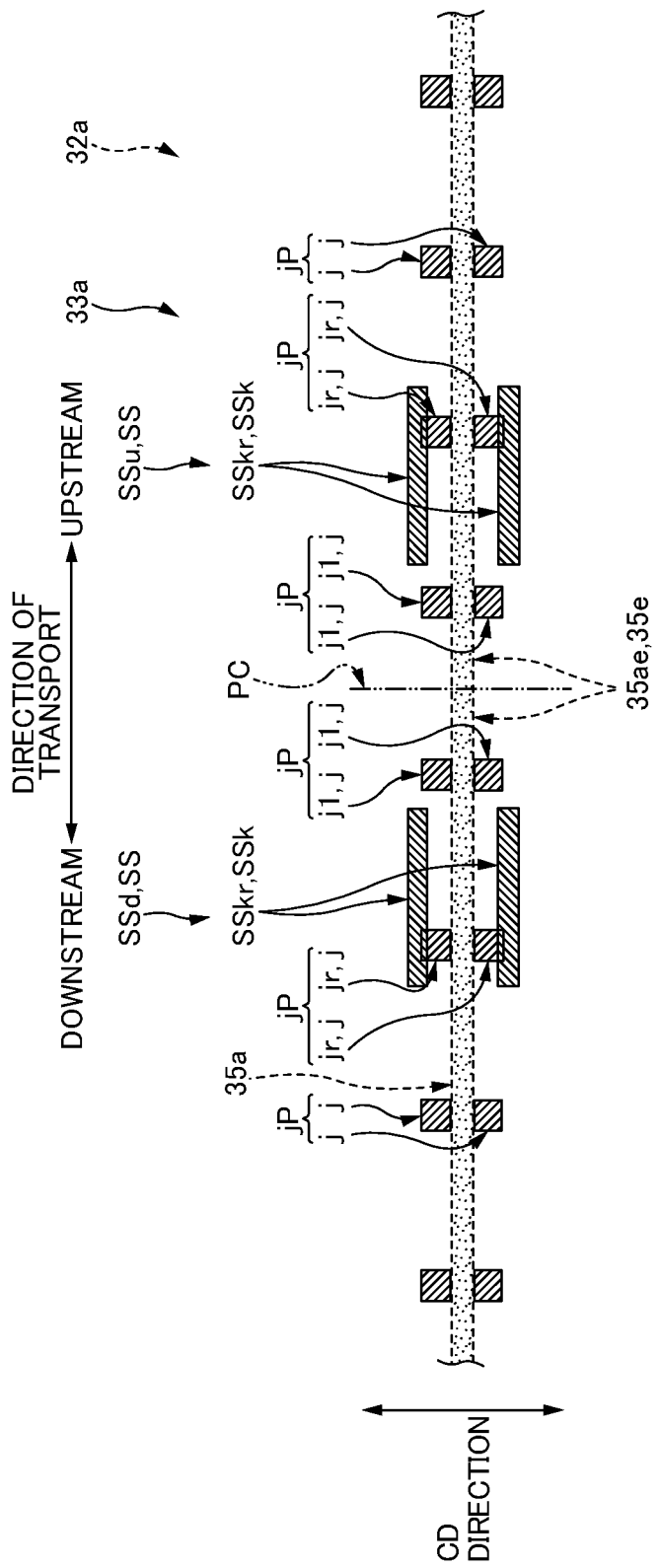
FIG. 12A is a schematic view of a case where welded portions j (j1) other than the overlapping-welded portions jr are provided at positions between the side-seal section SS and a cutting target position PC in the direction of transport.

Note that there is no limitation whatsoever to this. For example, as shown in FIG. 12A that will be described later, the welded portions j located closest to the cutting target position PC are not required to be overlapping-welded portions jr, and this similarly applies to the later-described example in FIG. 11B as well.

Also, the above-described effects can be suitably achieved as long as the overlapping-welded portions jr pertaining to at least one elastic-string continuous body 35a are in the above-described positional relationship. Accordingly, there is no need for the overlapping-welded portions jr, jr . . . pertaining to all of the elastic-string continuous bodies 35a, 35a . . . in FIG. 9C to be in the above-described positional relationship. For example, the overlapping-welded portions jr, jr . . . pertaining to one-third or more, half or more, or two-thirds or more of all of the elastic-string continuous bodies 35a, 35a may be in the above-described positional relationship, and this similarly applies to the later-described example in FIG. 11B as well.

Note that the arrangement of the overlapping-welded portions jr and the side-seal section SS in the positional relationship shown in FIG. 11A can be realized by setting the arrangement pattern of protrusion portions on the outer circumferential surface of a roll of the previously-described heat sealing device or ultrasonic sealing device provided at the first processing position PK1, and setting the arrangement pattern of protrusion portions on the outer circumferential surface of a roll of the previously-described heat sealing device or ultrasonic sealing device provided at the fourth processing position PK4, for example. This similarly applies to the realizing of such arranging in the examples in FIGS. 11B to 12B described below.

In the example in FIG. 11B as well, the welded portions j that are located closest to the cutting target position PC are overlapping-welded portions jr. Also, upstream ends jreu of the overlapping-welded portions jr in the direction of transport are located downstream in the direction of transport with respect to the central position CSS of the downstream side-seal section SSd in the direction of transport. More specifically, in this example, the overlapping-welded portions jr are located downstream in the direction of transport with respect to the central positions CSSkr of welded portions SSkr which are the welded portions SSk, SSk . . . of the downstream side-seal section SSd and which are overlapped with the overlapping-welded portions jr. This therefore makes it possible to more reliably suppress the above-described protrusion of the end portion 35e of the elastic string 35.

Also, at least one welded portion j (j1) is provided at a position between the side-seal section SS and the cutting target position PC in the direction of transport as shown in FIG. 12A. According to this configuration, after the cutting step is performed at the previously described fifth processing position PK5, the elastic string 35 is attached to the two nonwoven fabric sheets 32 and 33 pertaining to the front band member 31 due to being sandwiched and pressed by not only the above-described overlapping-welded portions jr but also by two welded portions j1. This makes it possible to more reliably suppress the case where a portion not having stretchability is formed in the range R31 that is inward in the lateral direction, which is the direction of transport, of the side-seal sections SS in the two nonwoven fabric sheets 32 and 33.

Figure 12B:
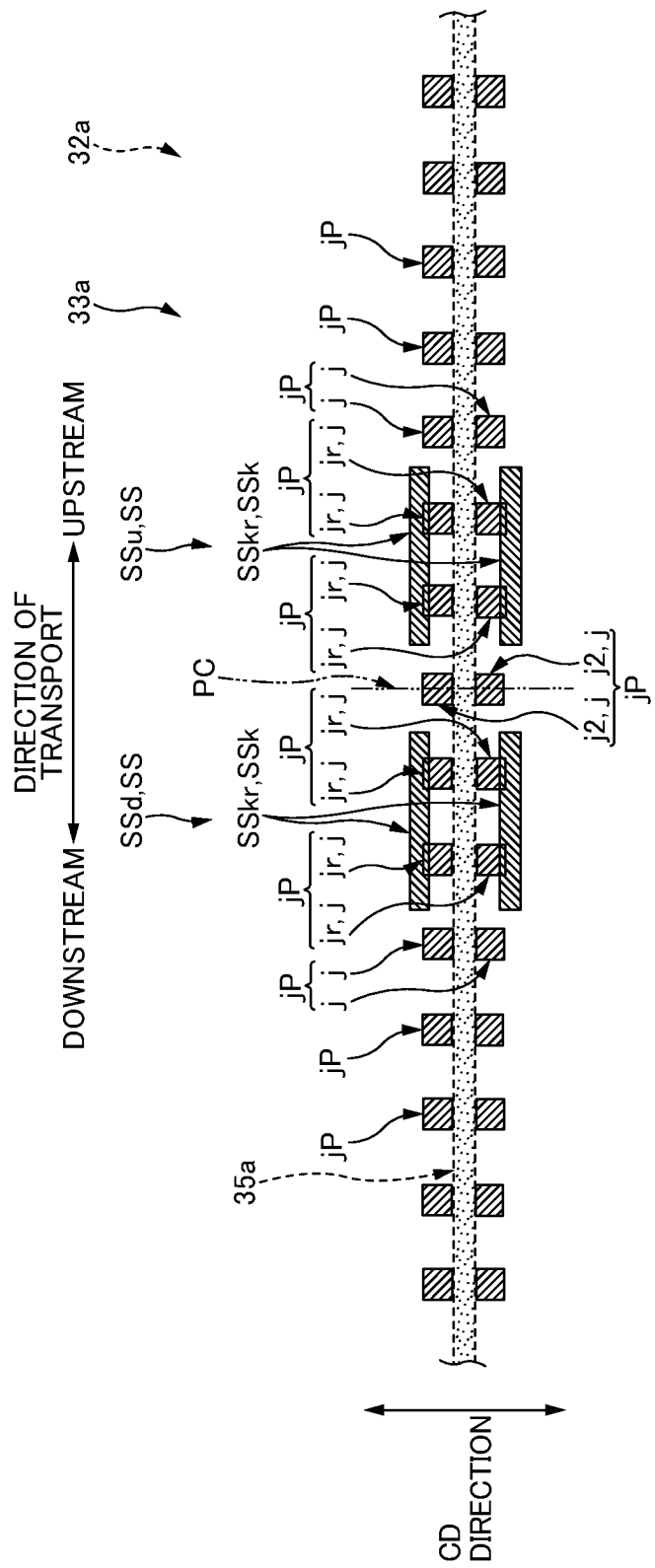
FIG. 12B is a schematic view of a case where welded portions j (j2) other than the overlapping-welded portions jr are provided so as to span the cutting target position PC in the direction of transport.

Furthermore, that at least one welded portion j (j2) other than a overlapping-welded portion jr is provided straddling the cutting target position PC in the direction of transport as shown in FIG. 12B. Even with this configuration, it is possible to achieve a suppress effect similar to that described above.

Also, in this example, the elastic-string continuous bodies 35a, 35a . . . are arranged side-by-side in the CD direction, and a pair of the previously described welded portions j are provided in correspondence with each of the elastic-string continuous bodies 35a as shown in FIG. 9B. Here, as shown in FIG. 13, the following configuration includes: concerning a welded portion SSk1 which is a farthest-located-on-one-side-in-CD-direction one of the welded portions SSk, SSk . . . in the side-seal section SS (this welded portion SSk1 corresponding to the "portion of the side-seal section that is farthest located on the one side in the CD direction"), at least one of the elastic-string continuous bodies 35a, 35a . . . is provided on the one side in the CD direction with respect to the welded portion SSk1; and the pair of welded portions j provided in correspondence with that elastic-string continuous body 35a are provided on the one side with respect to the welded portion SSk1. Hereinafter, these welded portions j will also be called "one-side welded portions j3 (corresponding to one-side joining portions)", and in this example in FIG. 13, the one side in the CD direction corresponds to the upper side in the vertical direction of the diaper 1. For this reason, the one-side welded portions j3 are formed in a portion that is to form the waist opening BH in the two continuous sheets 32a and 33a pertaining to the front band member 31.

According to this configuration, the one-side welded portions j3 make it possible to suppress the case where large portions in which the pair of facing surfaces of the two nonwoven fabric sheets 32 and 33 pertaining to the front band member 31 are not joined to each other are formed in the CD-direction end portions after the cutting step in the fifth processing position PK5. Accordingly, it is possible to suppress a separation of the pair of facing surfaces over a wide range due to such unjoined portions.

Figure 14:
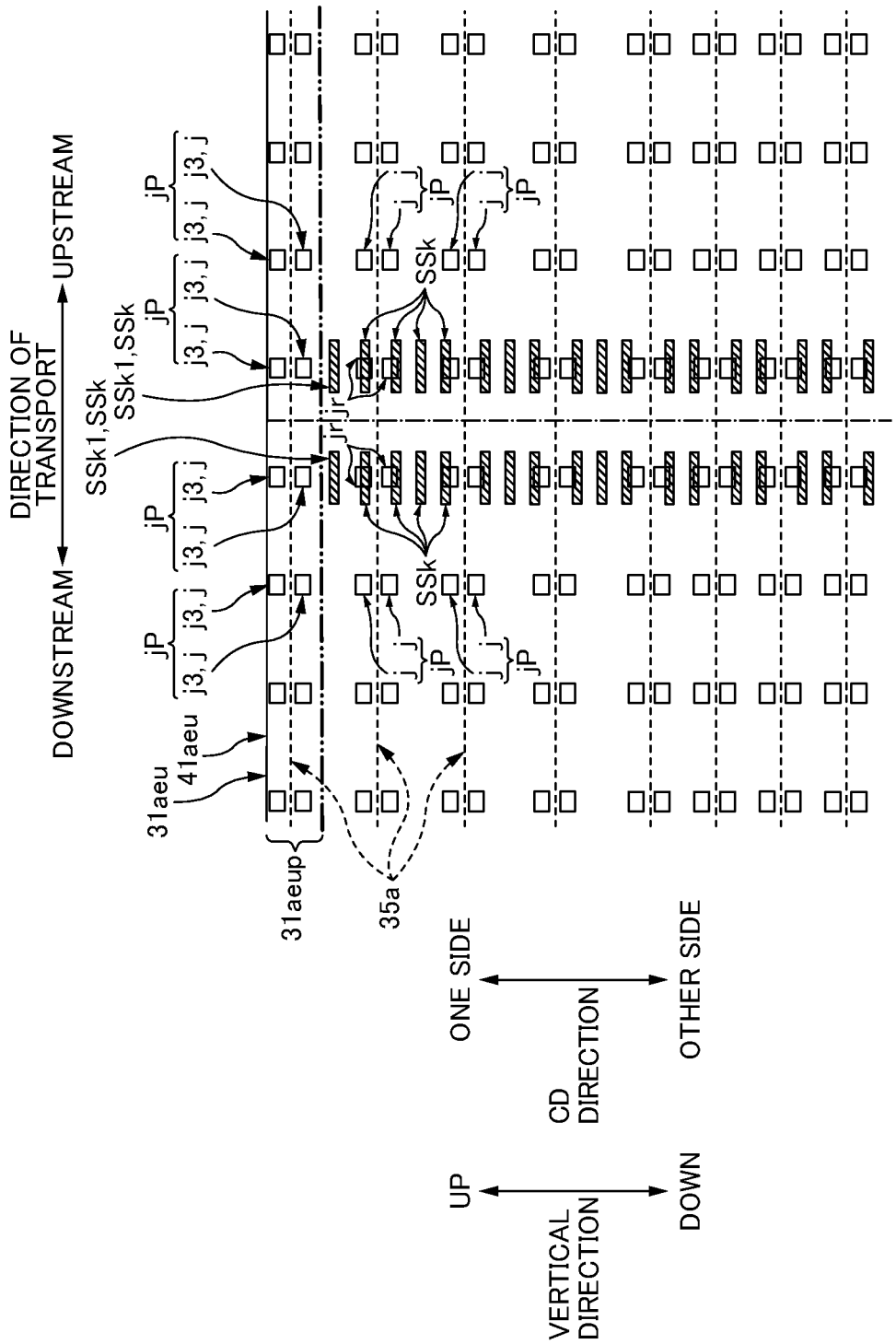
FIG. 14 is a schematic view of a case where end portions 31aeu in the CD direction of two continuous sheets 32a and 33a pertaining to the front band member 31 protrude to the one side in the CD direction beyond end portions 41aeu in the CD direction of two continuous sheets 42a and 43a pertaining to the back band member 41 in FIG. 13.

Also, in this regard, in the folding processing performed at the third processing position PK3 in FIG. 8, the two continuous sheets 32a and 33a pertaining to the front band member 31 and the two continuous sheets 42a and 43a pertaining to the back band member 41 are overlaid in the thickness direction such that, by design, the vertical upper end portion 31eu of the front band member 31 and the vertical upper end portion 41eu of the back band member 41 in FIG. 2 match each other in the vertical direction. Depending on the folding precision in this folding processing, there is produced, as shown in FIG. 14, a CD-direction shift between a pertaining-front-band-member end portion 31aeu and a pertaining-back-band-member end portion 41aeu; the end portion 31aeu corresponds to the upper end portion 31eu in the for-front-band-member continuous sheets 32a and 33a, and the end portion 41aeu corresponds to the upper end portion 41eu in the for-back-band-member continuous sheets 42a and 43a.

For example, there are cases where the end portion 31aeu of the two for-front-band-member-31 continuous sheets 32a and 33a protrude to the one side in the CD direction (i.e., the upper side in the vertical direction) with respect to the two for-back-band-member-41 continuous sheets 42a and 43a. In this case as well, in one or more embodiments as shown in FIG. 14, the previously described one-side welded portions j3 are provided in a protruding portion 31*aeup* in the end portion 31*aeu*.

According to this configuration, even if the end portion 31*aeu* of the two for-front-band-member-31 continuous sheets 32*a* and 33*a* protrudes to the one side in the CD direction due to the folding precision, it is possible to suppress the case where a large CD-direction portion in which the pair of facing surfaces of the continuous sheets 32*a* and 33*a* are not joined to each other is formed in the protruding portion 31*aeup* of the end portion 31*aeu*.

Figure 15:
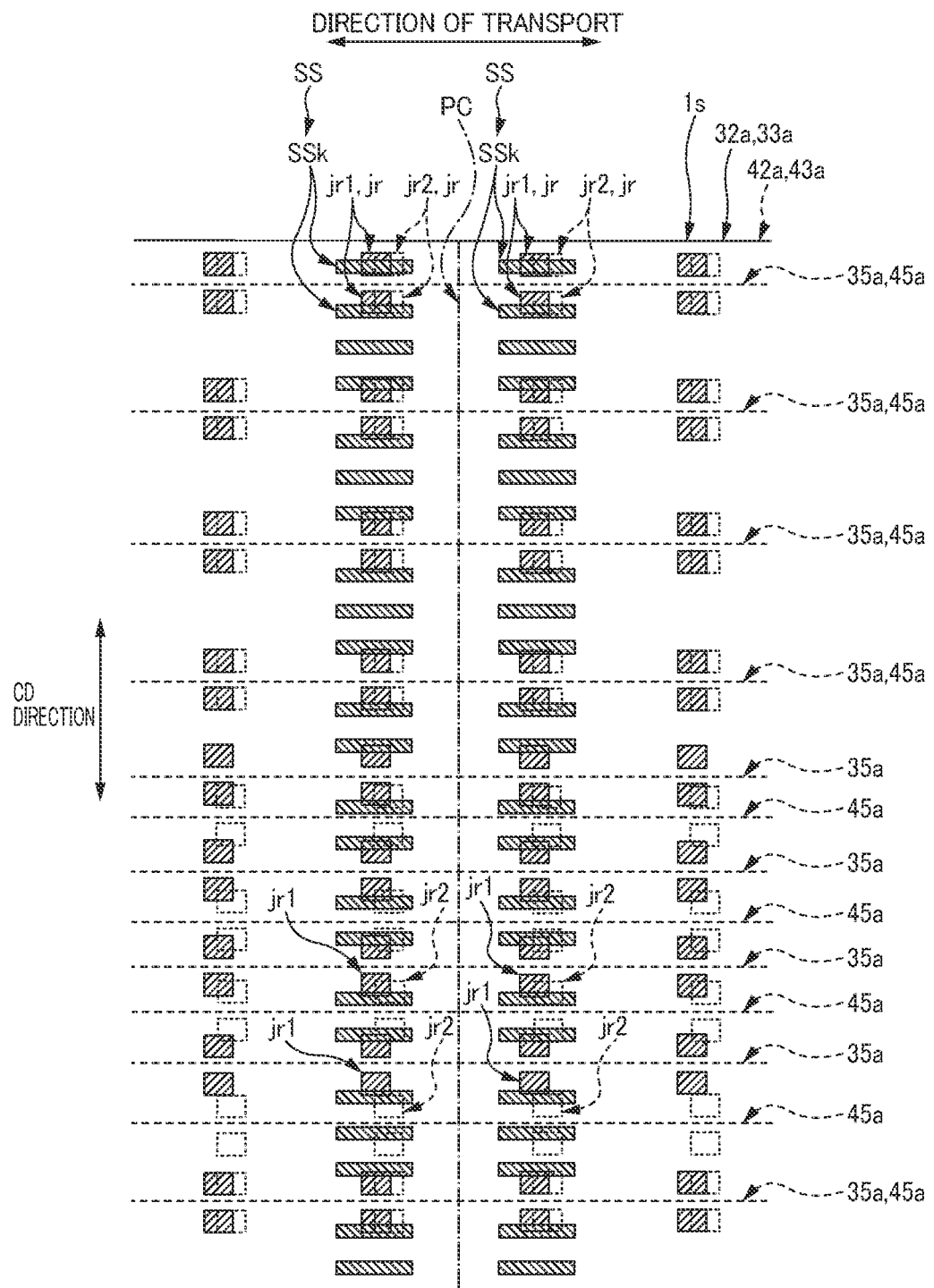
FIG. 15 is a schematic illustrative view of a positional relationship between overlapping-welded portions jr of the continuous sheets 32a and 33a pertaining to the front band member 31 and overlapping-welded portions jr of the continuous sheets 42a and 43a pertaining to the back band member 41.

FIG. 15 is a schematic illustrative view of a positional relationship between overlapping-welded portions jr of the continuous sheets 32*a* and 33*a* pertaining to the front band member 31 and overlapping-welded portions jr of the continuous sheets 42*a* and 43*a* pertaining to the back band member 41. Specifically, FIG. 15 is a schematic plan view of the underpants-shaped-disposable-diaper continuous body is that is transported between the fourth processing position PK4 and the fifth processing position PK5 in the manufacturing line (FIG. 8). More specifically, it is a schematic view of the cutting target position PC and the vicinity thereof in the continuous body is as viewed from the front band member 31 side in the thickness direction.

As shown in FIG. 15, first, the elastic-string continuous bodies 35*a* of the front band member 31 and the elastic-string continuous bodies 45*a* of the back band member 41 are overlapped in the thickness direction at several locations in the CD direction, whereas at several other locations, there are only the elastic-string continuous bodies 35*a* of the front band member 31, and at still other locations there are only the elastic-string continuous bodies 45*a* of the back band member 41 are provided.

Also, here, letting the overlapping-welded portions jr formed in the continuous sheets 32*a* and 33*a* pertaining to the front band member 31 be called "first overlapping-welded portions jr1" (corresponding to first overlapping-joining portions), and letting the overlapping-welded portions jr formed in the continuous sheets 42*a* and 43*a* pertaining to the back band member 41 be called "second overlapping-welded portions jr2" (corresponding to second overlapping-joining portions), in this example, as shown in FIG. 15, all of the first overlapping-welded portions jr1 are shifted in the direction of transport or the CD direction with respect to the second overlapping-welded portions jr2 that are closest to the first overlapping-welded portions jr1.

Specifically, in this example, all of the first overlapping-welded portions jr1, jr1 . . . are shifted in the direction of transport with respect to the second overlapping-welded portions jr2 that are closest thereto. Also, several of the first overlapping-welded portions jr1, jr1 . . . are shifted in the CD direction as well with respect to the corresponding second overlapping-welded portions jr2, and several of those first overlapping-welded portions jr1 are shifted not being overlapped at all with the corresponding second overlapping-welded portions jr2.

According to this configuration, it is possible to suppress a stiffness that can occur if the first overlapping-welded portions jr1 and the second overlapping-welded portions jr2 are completely overlapped, that is to say a stiffness of the side-seal sections SS of the diaper 1 will vary greatly, which is likely to cause the person touching those portions to feel discomfort.

Note that there is no limitation whatsoever to this. Specifically, it is possible to suitably achieve the above-described effect of suppressing variation in stiffness as long as at least one, one-third or more, half or more, or two-thirds or more of all of the first overlapping-welded portions jr1, jr1 . . . are shifted in the direction of transport or the CD direction with respect to the closest second overlapping-welded portion jr2. Also, the shifted first overlapping-welded portion jr1 does not need to be shifted in both the direction of transport and the CD direction. In other words, the first overlapping-welded portion jr1 may be shifted in the direction of transport and not in the CD direction, or conversely, may be shifted in the CD direction and not in the direction of transport, and such first overlapping-welded portions jr1 are also shown in the example in FIG. 15.

Also, the above-described CD-direction shifting of the first overlapping-welded portions jr1 can be realized by adjusting in the CD direction the folding position at which the approximately ladder-shaped diaper continuous body 1*hs* is folded at the third processing position PK3; the folding position is a predetermined position in the CD direction. Specifically, adjusting the predetermined position in the CD direction causes to adjust the relative positions in the CD direction of the for-back-band-member-41 continuous sheets 42*a* and 43*a* relative to the for-front-band-member-31 continuous sheets 32*a* and 33*a*, and this makes it possible to reliably achieve the aforementioned positional shifting.

Furthermore, the above-described direction-of-transport shifting of the first overlapping-welded portion jr1 can be realized by adjusting the rotation-direction phases of the following rolls: the first one is a roll of the previously described heat sealing device or ultrasonic sealing device arranged at the first processing position PK1, and has protrusions; and the second one is a roll of the previously described heat sealing device or ultrasonic sealing device arranged at the fourth processing position PK4, and has protrusions.

Although embodiments of the present invention have been described hereinabove, the above embodiments of the present disclosure are simply to facilitate understanding of the present disclosure and are not in any way to be construed as limiting the present disclosure. The present disclosure may variously be changed or altered without departing from its gist and encompass equivalents thereof. For example, modification which will be described below is possible.

In the above embodiments, the welded portion j is illustrated as an example of the joining portion (second joining portion) that joins together the mutually-opposing pair of facing surfaces of the two nonwoven fabric sheets 32 and 33 (42 and 43) as shown in FIG. 5, but there is no limitation whatsoever to this. For example, according to one or more embodiments, the joining portion (second joining portion) may be formed using an adhesive, and in this case, the adhesive is selectively applied, on at least one of the two facing surfaces, to a target formation position at which the joining portion (second joining portion) is to be formed.

In the above embodiments, two continuous sheets 32*a* and 33*a* (42*a* and 43*a*) are illustrated as examples of the first sheet-like-member continuous body (second sheet-like-member continuous body) as shown in FIG. 8, but there is no limitation whatsoever to this. For example, according to one or more embodiments, the first sheet-like-member continuous body (second sheet-like-member continuous body) may be constituted by one continuous sheet. In this case, the pair of facing surfaces are formed by folding one continuous sheet at a predetermined position in the CD direction, and then inserting the elastic-string continuous bodies 35*a* (45*a*) between the pair of facing surfaces.

In the above embodiments, the elastic strings 35 (45) are illustrated as examples of elastic members (second elastic members), and the elastic-string continuous bodies 35a (45a) are illustrated as examples of the elastic-member continuous bodies (continuous bodies of the second elastic member), but according to one or more embodiments spandex and the like are other specific examples of such elastic strings 35 (45), and LYCRA (registered trademark) is an example of such a product. Also, the elastic strings 35 (45) can have a fiber density of 400 dtex to 1,000 dtex, for example. Furthermore, rubber strips may be used as the elastic members (second elastic members), and rubber strip continuous bodies may be used as the elastic-member continuous bodies (second elastic-member continuous bodies).

In the above embodiments, as shown in FIG. 5, all of the elastic strings 35, 35 . . . provided in the front band member 31 are arranged so as to be continuous over substantially the entire length in the lateral direction, but there is no limitation whatsoever to this. For example, according to one or more embodiments, several of the elastic strings 35, 35 . . . may be discontinuous at a central position in the lateral direction for example. Note that the same applies to the elastic strings 45, 45 . . . of the back band member 41 as well.

In the above embodiments, as shown in FIG. 3, the three-piece type of disposable diaper 1 is illustrated as an example of the absorbent article, but there is no limitation whatsoever to this. For example, the method of one or more embodiments of the present invention may be used when attaching elastic members such as elastic strings to a sheet-like member for use in a two-piece type of disposable diaper. A two-piece type disposable diaper is a type of diaper that has a first component and a second component: the first component is an exterior sheet having a two-layer structure and including a front portion, a crotch portion, and a back portion; and the second component is the absorbent main body 10 fixed to the skin-side surface of the exterior sheet.

In the above embodiments, the welded portion j having an approximately square shape in a plan view is illustrated as an example of the joining portion (second joining portion) as shown in FIG. 6, but the shape of the welded portion j is not limited in any way to this. For example, according to one or more embodiments, a circular shape may be applied, or an elongated shape having a longitudinal direction, such as a rectangular or oval shape, may be used. Note that in the latter case of a shape having a longitudinal direction, the longitudinal direction may conform to the direction of transport (lateral direction), may conform to the CD direction (vertical direction), or may conform to a direction that intersects both the direction of transport and the CD direction.

In the above embodiments, as shown in FIG. 5, the welded portions j, j . . . (including the overlapping-welded portions jr) are provided in a so-called ladder-like arrangement that is defined in the lateral direction and the vertical direction (longitudinal direction). Specifically, according to one or more embodiments, the welded portions j, j . . . are provided at intersections between virtual lines extending in the lateral direction and virtual lines extending in the vertical direction, but there is no limitation whatsoever to this. For example, the welded portions j, j . . . may be provided in a so-called staggered arrangement by being providing at positions that are shifted in the lateral direction from the aforementioned intersections. Also, although the welded portions j, j . . . are arranged side-by-side in the vertical direction in FIG. 5, there is no limitation whatsoever to this. For example, the welded portions j, j . . . may be arranged side-by-side in a diagonal direction that intersects both the vertical direction and the lateral direction.

Also, in the example in FIG. 5, the two overlapping-welded portions jr that form the overlapping-welded portion pair jrP are provided at the same position as each in the lateral direction (direction of transport), but there is no limitation whatsoever to this. For example, the positions of the two overlapping-welded portions jr may be shifted from each other in the lateral direction (direction of transport) as long as the elastic string 35 (45) can be sandwiched and pressed. Also, the virtual straight line on which the two overlapping-welded portions jr are to be aligned is not required to extend in the CD direction, and may be inclined from the CD direction at a predetermined angle other than 90°. Note that this similarly applies to the welded portions j, j . . . other than the overlapping-welded portions jr as well.

In the above embodiments, as shown in FIG. 5, a welded portion j is not provided between two welded portion pairs jP that are adjacent in the vertical direction (CD direction), but there is no limitation whatsoever to this. For example, according to one or more embodiments, one or more welded portions j may be provided between two welded portion pairs jP. Note that such a welded portion j does not contribute to attachment of the elastic strings 35 (45) to the nonwoven fabric sheets 32 and 33 (42 and 43), and only contributes to the joining of the nonwoven fabric sheets 32 and 33 (42 and 43) to each other.

In the above embodiments, the elastic strings 35 (45) attempt to contract in the direction of transport and expand in the CD direction due to the cutting performed in the cutting step at the fifth processing position PK5, but are sandwiched and pressed in the CD direction between pairs of welded portions j, and the elastic strings 35 (45) are thus attached to the two nonwoven fabric sheets 32 and 33 (42 and 43). However, there is no limitation whatsoever to this. Specifically, according to one or more embodiments, a configuration is possible in which, at a stage before the cutting step, the elastic-string continuous bodies 35a (45a), which have been inserted between the pair of facing surfaces of the continuous sheets 32a and 33a (42a and 43a) pertaining to the two nonwoven fabric sheets 32 and 33 (42 and 43), are allowed to relax from the stretched state such that the continuous bodies 35a (45a) contract in the direction of transport, and thus the continuous bodies 35a (45a) are sandwiched and pressed in the CD direction between the pair of welded portions j. For example, a configuration is possible in which the elastic-string continuous bodies 35a (45a) in the underpants-shaped diaper continuous body is in FIG. 8 are allowed to relax from the stretched state such that the continuous bodies 35a (45a) contract in the direction of transport, and thus the continuous bodies 35a (45a) are sandwiched and pressed in the CD direction between the pair of welded portions j. Subsequently, the underpants-shaped diaper continuous body is may be cut in the cutting step, thus producing the diaper 1.

In the above embodiments, in addition to the nonwoven fabric sheets 32 and 33 that are to be produced by cutting the two continuous sheets 32a and 33a (an example of the first sheet-like-member continuous body), the nonwoven fabric sheets 42 and 43 that are produced by cutting the two continuous sheets 42a and 43a (an example of the second sheet-like-member continuous body) also include the elastic strings 45 (the second elastic members) attached thereto by being sandwiched and pressed between pair of welded portions j (second joining portions). However, there is no limitation whatsoever to this. In other words, in the nonwoven fabric sheets 42 and 43, the elastic strings 45 may be attached by not only being sandwiched and pressed between pairs of welded portions j, but also by the adhesive. Also, in the nonwoven fabric sheets 42 and 43, the overlapping-welded portions jr are not required to be provided, that is to say, the second elastic members such as the elastic strings 45 can also be omitted from the nonwoven fabric sheets 42 and 43.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 disposable diaper (absorbent article),
1hs approximately ladder-shaped diaper continuous body,
1hsb folded diaper continuous body,
1s underpants-shaped diaper continuous body,
10 absorbent main body, 10ea end portion, 10eb end portion,
11 absorbent body, 11c absorbent core,
13 top sheet, 15 back sheet,
17 elastic string (elastic member), 18 elastic string (elastic member),
31 front band member, 31e end portion, 31eu upper end portion,
31aeu end portion, 31aeup protruding portion,
32 nonwoven fabric sheet, 32a continuous sheet,
33 nonwoven fabric sheet, 33a continuous sheet,
35 elastic string (elastic member), 35e end portion,
35a elastic-string continuous body (elastic-member continuous body),
35ae portion,
41 back band member, 41e end portion, 41eu upper end portion,
41aeu end portion,
42 nonwoven fabric sheet, 42a continuous sheet,
43 nonwoven fabric sheet, 43a continuous sheet,
45 elastic string (second elastic member), 45e end portion,
45a elastic-string continuous body (second elastic-member continuous body),
j welded portion (joining portion, second joining portion),
jr overlapping-welded portion (overlapping-joining portion), jreu upstream end,
jr1 first overlapping-welded portion (first overlapping-joining portion),
jr2 second overlapping-welded portion (second overlapping-joining portion),
jP welded portion pair,
j1 welded portion (joining portion), j2 welded portion (joining portion),
j3 one-side welded portion (one-side joining portion),
BH waist opening, LH leg opening,
LG leg gather, LSG barrier cuff,
SS side-seal section, SSeu upstream end, SSed downstream end,
SSd downstream side-seal section, SSdeu upstream end,
SSu upstream side-seal section,
SSk welded portion, SSkeu upstream end, SSked downstream end,
SSkr welded portion, SSkreu upstream end, SSk1 welded portion,
CL1 central position (predetermined position), CSSkr central position,
PC cutting target position, PBL boundary position,
PK1 first processing position, PK2 second processing position, PK3 third processing position,
PK4 fourth processing position, PK5 fifth processing position,
R31 region, R31e end portion, R41 region, R41e end portion

What is claimed is:

1. A method for manufacturing an absorbent article that comprises a first sheet member, a second sheet member, a first elastic member, and side-seal sections, wherein the elastic first member is attached to the first sheet member, the first sheet member is stretchable in a lateral direction using the first elastic member, the side-seal sections are disposed at each lateral end portion of the absorbent article, the first sheet member and the second sheet member are overlaid in a thickness direction and welded together at the side-seal sections, and the thickness direction intersects the lateral direction, the method comprising:

arranging first elastic-member continuous bodies between a pair of mutually-opposing facing surfaces of a first sheet member continuous body that is transported in a transport direction that is the same as the lateral direction, wherein
the first elastic-member continuous bodies and the first sheet member continuous body are arranged continuously in the transport direction, and
the first elastic-member continuous bodies are in a stretched state in the transport direction and spaced side-by-side in a CD direction that intersects the transport direction and the thickness direction;

disposing first welding portions spaced apart in the transport direction and the CD direction on the first sheet member continuous body, wherein
the welding portions join the pair of mutually-opposing facing surfaces of the first sheet member continuous body,
the first welding portions are disposed on two sides of the first elastic-member continuous bodies in the CD direction while the first elastic-member continuous bodies are maintained in the stretched state,
the welding portions are disposed so that, by direction-of-transport contraction and CD-direction expansion of the first elastic member after cutting of the absorbent article, the first elastic member is sandwiched and pressed in the CD direction by the first welding portions on the two sides of the first elastic-member continuous bodies, and
the first welding portions are disposed so that a portion of at least one of the first welding portions overlaps with at least a portion of the side-seal sections in a thickness direction of the first sheet member continuous body;

overlaying, in the thickness direction, a second sheet member continuous body on the first sheet member continuous body where first the welding portions are disposed, wherein the second sheet member continuous body is arranged continuously in the transport direction;

disposing, in the transport direction, the side-seal sections on each of two sides of cutting target positions spaced apart at a predetermined pitch in the transport direction on the first sheet member continuous body, wherein the first sheet member continuous body and the second sheet member continuous body are welded together at the side-seal sections; and the cutting of the absorbent article, after the disposing of the side-seal sections, by cutting the first sheet member continuous body, the first elastic-member continuous bodies, and the second sheet member continuous body at the cutting target positions.

2. The method according to claim 1, wherein at least one of the first welding portions is disposed between one of the side-seal sections and one of the cutting target positions in the transport direction.

3. The method according to claim 1, wherein
the at least one of the first welding portions that overlaps with the side-seal sections is a first overlapping-joining portion, and
at least one of the first welding portions other than the first overlapping-joining portion straddles one of the cutting target positions in the transport direction.

4. The method according to claim 1, wherein
the first welding portions are disposed for each of the first elastic-member continuous bodies,
at least one of the first elastic-member continuous bodies are disposed farther than an endmost portion of the side-seal sections in one direction along the CD direction, and
the first welding portions of the at least one first elastic-member continuous body are disposed farther than the endmost portion of the side-seal sections in the one direction.

5. The method according to claim 4, wherein
each of the first welding portions disposed farther than the endmost portion of the side-seal sections is a one-side joining portion, and
the first sheet member and the second sheet member are overlaid such that the first sheet member has a portion in which the one-side joining portion is disposed and that protrudes farther than an end of the second sheet member in the one direction.

6. The method according to claim 1, wherein in the first sheet member continuous body and the second sheet member continuous body, an adhesive is not provided in a portion where the side-seal sections are disposed.

7. The method according to claim 1, wherein
a second elastic member is attached to the second sheet member,
the second sheet member is stretchable in the lateral direction using the second elastic member,
the method further comprises:
arranging second elastic-member continuous bodies between a pair of mutually-opposing facing surfaces of the second sheet member continuous body, wherein
the second elastic-member continuous bodies are arranged continuously in the transport direction, and
the second elastic-member continuous bodies are in the stretched state and spaced side-by-side in the CD direction;
disposing second welding portions spaced apart on the second sheet member continuous body in the transport direction and the CD direction, wherein
the second welding portions join the pair of mutually-opposing facing surfaces of the second sheet member continuous body,
the second welding portions are disposed on two sides of the second elastic-member continuous bodies in the CD direction while the second elastic-member continuous bodies are maintained in the stretched state,
the second welding portions are disposed so that, by direction-of-transport contraction and CD-direction expansion of the second elastic member after the cutting of the absorbent article, the second elastic member is sandwiched and pressed in the CD direction by the second welding portions on the two sides of the second elastic-member continuous bodies, and
the second welding portions are disposed so that a portion of at least one of the second welding portions overlaps with at least a portion of the side-seal sections in a thickness direction of the second sheet member continuous body;
in the overlaying of the second sheet member continuous body on the first sheet member continuous body, overlaying the second welding portions on the first welding portions; and
in the cutting of the absorbent article, further cutting the second elastic-member continuous bodies at the cutting target positions.

8. The method according to claim 7, wherein
the at least one of the second welding portions that overlaps with the side-seal sections is a second overlapping-joining portion,
the second sheet member continuous body and the first sheet member continuous body are overlaid such that the first overlapping-joining portion is shifted in the transport direction or the CD direction with respect to the second overlapping-joining portion closest to the first overlapping-joining portion.

9. The method according to claim 1, wherein
the at least one of the first welding portions that overlaps with the side-seal sections is a first overlapping-joining portion,
a downstream one of the side-seal sections disposed on two sides of the cutting target positions in the transport direction is a downstream side-seal section,
the first overlapping-joining portion overlaps with the downstream side-seal section, and
in the transport direction, an upstream end of the first overlapping-joining portion located downstream with respect to an upstream end of the downstream side-seal section.

10. The method according to claim 9, wherein in the transport direction, the upstream end of the first overlapping-joining portion is located downstream with respect to a central position of the downstream side-seal section.

11. The method according to claim 1, wherein
at least two of the first welding portions are disposed at a predetermined formation pitch in the transport direction to span and extend beyond the side-seal sections and the cutting target positions in the transport direction, and
a size of the predetermined formation pitch is smaller than a direction-of-transport size of the side-seal sections.

* * * * *